United States Patent
Blanchard et al.

(10) Patent No.: US 10,342,704 B2
(45) Date of Patent: Jul. 9, 2019

(54) SPORT GOGGLES AND ADAPTORS FOR SPORT GOGGLES

(71) Applicant: 100% SPEEDLAB, LLC, San Diego, CA (US)

(72) Inventors: Marc Guy Blanchard, San Diego, CA (US); Ludovic Francis Boinnard, San Diego, CA (US); Kevin Michael Sigismondo, San Diego, CA (US); Jonathan Knight, Lisburn (IE)

(73) Assignee: 100% SPEEDLAB, LLC, San Diego, CA (US)

( * ) Notice: Subject to any disclaimer, the term of this patent is extended or adjusted under 35 U.S.C. 154(b) by 40 days.

(21) Appl. No.: 14/701,379

(22) Filed: Apr. 30, 2015

(65) Prior Publication Data
US 2015/0320600 A1    Nov. 12, 2015

Related U.S. Application Data

(60) Provisional application No. 61/989,801, filed on May 7, 2014.

(51) Int. Cl.
*A61F 9/02* (2006.01)
*A63B 71/10* (2006.01)

(52) U.S. Cl.
CPC .............. *A61F 9/029* (2013.01); *A61F 9/025* (2013.01); *A61F 9/026* (2013.01); *A61F 9/028* (2013.01); *A63B 71/10* (2013.01)

(58) Field of Classification Search
CPC .......... A61F 9/025; A61F 9/026; A61F 9/028; A61F 9/029; A63B 71/10
See application file for complete search history.

(56) References Cited

U.S. PATENT DOCUMENTS

| | | | | |
|---|---|---|---|---|
| 3,946,442 A | * | 3/1976 | Wallander | A42B 3/26 2/9 |
| 4,428,081 A | * | 1/1984 | Smith | A61F 9/025 2/422 |
| 4,528,701 A | * | 7/1985 | Smith | A61F 9/02 2/438 |
| 4,689,838 A | * | 9/1987 | Angermann | G02C 1/08 2/436 |
| 4,748,697 A | * | 6/1988 | Hodnett | A61F 9/025 2/438 |

(Continued)

FOREIGN PATENT DOCUMENTS

| | | |
|---|---|---|
| CA | 2290295 A1 | 7/2014 |
| WO | WO 2005/107667 | 11/2005 |
| WO | WO 2008/045317 A2 | 4/2008 |

*Primary Examiner* — Anne M Kozak
(74) *Attorney, Agent, or Firm* — Haynes and Boone, LLP

(57) ABSTRACT

A goggle frame and an adaptor configured to attach to the goggle frame are disclosed in accordance with various embodiments. The adaptor may allow the goggle frame to adapt to different lenses or accessories. In particular, the adaptor may allow the goggle frame to adapt to lenses of different sizes, thicknesses, shapes, shades, colors, prescriptions, curvatures, and the like. Further, the adaptor may allow the goggle frame to adapt to various accessories, such as roll-off film systems of different sizes, various imaging devices, e.g., cameras, video cameras, display devices, e.g., LCD or LED displays, heads up displays, lighting devices, Global Positioning Systems (GPS), and the like.

13 Claims, 21 Drawing Sheets

(56) References Cited

U.S. PATENT DOCUMENTS

| | | | | |
|---|---|---|---|---|
| 5,163,185 A * | 11/1992 | Hodnett | A62B 18/082 | 2/422 |
| 5,203,035 A * | 4/1993 | Lawlor | A62B 18/082 | 2/434 |
| 5,410,763 A * | 5/1995 | Bolle | A61F 9/025 | 2/436 |
| 5,657,106 A * | 8/1997 | Herald, Jr. | A61F 9/025 | 2/437 |
| 5,809,580 A * | 9/1998 | Arnette | A61F 9/027 | 2/426 |
| 6,009,564 A * | 1/2000 | Tackles | A61F 9/02 | 2/436 |
| 6,047,412 A * | 4/2000 | Wilson, II | A61F 9/025 | 2/422 |
| 6,073,296 A * | 6/2000 | Bouguerfa | A42B 3/26 | 15/102 |
| 6,282,727 B1 * | 9/2001 | Lindahl | A61F 9/025 | 2/428 |
| 6,415,452 B1 * | 7/2002 | Watanabe | A61F 9/025 | 2/438 |
| 6,416,177 B1 * | 7/2002 | Gibson | A61F 9/02 | 2/438 |
| 6,601,240 B2 * | 8/2003 | Tsubooka | A61F 9/028 | 2/436 |
| 6,611,966 B1 * | 9/2003 | Yamamoto | A61F 9/028 | 2/436 |
| 6,637,877 B1 * | 10/2003 | Hartley | A61F 9/022 | 351/44 |
| 6,725,467 B2 * | 4/2004 | Harding | A61F 9/025 | 2/435 |
| 8,083,344 B2 * | 12/2011 | Blanshay | G02C 9/00 | 2/436 |
| 8,408,695 B2 * | 4/2013 | Calilung | G02C 1/06 | 351/137 |
| 8,458,823 B2 | 6/2013 | Matera | | |
| D687,480 S * | 8/2013 | Castro | D16/312 | |
| D687,881 S * | 8/2013 | Ginther | D16/312 | |
| D691,652 S * | 10/2013 | Castro | D16/311 | |
| D755,278 S * | 5/2016 | Blanchard | D16/311 | |
| 2012/0137398 A1 * | 6/2012 | Arnold | A61F 9/025 | 2/10 |
| 2012/0137414 A1 * | 6/2012 | Saylor | A61F 9/025 | 2/435 |
| 2012/0236250 A1 | 9/2012 | Yang | | |
| 2013/0104299 A1 * | 5/2013 | Chen | A61F 9/029 | 2/431 |
| 2014/0033408 A1 | 2/2014 | Currens et al. | | |
| 2014/0189943 A1 | 7/2014 | Tobia | | |

* cited by examiner

SPORT GOGGLES AND ADAPTORS FOR SPORT GOGGLES

CROSS-REFERENCE TO RELATED APPLICATION

This patent application claims the benefit of and priority to U.S. Provisional Patent Application No. 61/989,801, filed May 7, 2014 and entitled "Sport Goggles and Adaptors for Sport Goggles," which is hereby incorporated by reference in its entirety.

TECHNICAL FIELD

One or more embodiments relate generally to sport goggles and, more particularly, to adaptors for sport goggles.

BACKGROUND

Sport goggles are worn by users for various sports or activities, such as motorsports, powersports, snowsports, watersports, biking, or the like, to protect users' eyes. A sport goggle typically includes a goggle frame which is compatible with a specific type of lens or accessories. For example, a goggle may have a lens that is compatible with a 30 mm roll-off film. As such, the goggle is not compatible with a 45 mm roll-off film, because the 45 mm roll-off film would not be able to ride on the lens of the goggle completely due to size difference or because the canister for the 45 mm roll-off film would not be able to be attached properly to the lens of the goggle. Thus, the user would have to purchase another goggle that is compatible with the 45 mm roll-off film if the user wishes to use the 45 mm roll-off film.

SUMMARY

Goggle systems and methods are provided in accordance with one or more embodiments that are adaptable to different lenses and accessories. In particular, an adaptor is provided to attach to a goggle frame and to adapt the goggle frame for use with different lenses and accessories. The adaptor may adapt the goggle frame to lenses of different sizes, shapes, thicknesses, curvatures, colors, prescriptions, and the like. In some embodiments, the adaptor may adapt the goggle frame to attach different accessories, such as roll-off or tear-off film systems of different sizes, imaging devise, lighting devices, display devices, or the like. Accordingly, the adaptor may provide cost efficiency and usability of a goggle frame.

In accordance with an embodiment, a goggle may include a goggle frame and an adaptor. The goggle frame may include a first lens receiving portion configured to receive a first goggle lens. The adaptor may include a second lens receiving portion configured to receive a second goggle lens and an attachment portion configured to attach the adaptor to the first lens receiving portion of the goggle frame.

In accordance with an embodiment, one or more of a size, a curvature, a shape, a thickness, and a prescription of the second goggle lens received at the second lens receiving portion of the adaptor may be different from that of the first goggle lens receivable by the first lens receiving portion of the goggle frame.

In accordance with an embodiment, the first lens receiving portion of the goggle frame may include a ridge formed continuously around the goggle frame at an inner side of the goggle frame and a groove formed on the ridge continuously around the goggle frame at the inner side of the goggle frame. The attachment portion of the adaptor may include a rib formed continuously around the adaptor at an outer side of the adaptor. The rib of the adaptor may be accommodated in the groove formed on the ridge of the goggle frame when the adaptor is attached to the goggle frame.

In accordance with an embodiment, the attachment portion of the adaptor further may include a sloping wall connecting the rib to the second lens receiving portion of the adaptor. The rib and the sloping wall of the adaptor may form a V-shaped recess extending continuously around the adaptor. The V-shaped recess of the adaptor may be configured to accommodate the ridge of the goggle frame when the adaptor is attached to the goggle frame.

In accordance with an embodiment, a goggle adaptor may include a lens receiving portion configured to receive a goggle lens and an attachment portion configured to attach the goggle adaptor to a goggle frame. The attachment portion may be configured to attach to a lens receiving portion of the goggle frame. The attachment portion of the goggle adaptor may include a rib formed continuously around the goggle adaptor at an outer side of the goggle adaptor and a sloping wall connecting the rib to the lens receiving portion of the goggle adaptor. The rib and the sloping wall of the goggle adaptor may form a V-shaped recess extending continuously around the goggle adaptor. A thickness of the rib may correspond to a thickness of a lens receivable by the goggle frame. The rib may include cutouts positioned at predetermined intervals of the rib around the goggle adaptor. The cutouts may be configured to increase a deformability of the rib.

In accordance with an embodiment, a method for implementing a goggle adaptor is disclosed. The method may include attaching a goggle adaptor to a first lens receiving portion of a goggle frame, and attaching a lens to the goggle adaptor, wherein the lens is different from a lens that is receivable by the first lens receiving portion of the goggle frame. The method also may include attaching an accessory to one of the lens and the goggle adaptor.

The scope of the invention is defined by the claims, which are incorporated into this Summary by reference. A more complete understanding of embodiments of the invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

Embodiments of the invention and their advantages are best understood by referring to the detailed description that follows. It should be appreciated that like reference numerals are used to identify like elements illustrated in one or more of the Figures.

DETAILED DESCRIPTION

A goggle frame and an adaptor configured to attach to the goggle frame are disclosed in accordance with various embodiments. The adaptor may allow the goggle frame to adapt to different lenses or accessories. In particular, the adaptor may allow the goggle frame to adapt to lenses of different sizes, thicknesses, shapes, shades, colors, prescriptions, curvatures, and the like. Further, the adaptor may allow the goggle frame to adapt to various accessories, such as roll-off film systems of different sizes, various imaging devices, e.g., cameras, video cameras, display devices, e.g., LCD or LED displays, heads-up displays, lighting devices, Global Positioning Systems (GPS), and the like.

According to an embodiment, the adaptor may include an attachment portion configured to attach to a lens receiving portion of the goggle frame. The adaptor also may include a lens receiving portion that is configured to receive a lens that is different from a lens that is receivable by the lens receiving portion of the goggle frame. As such, roll-off film systems of different sizes may be attached to the goggle frame via the adaptor.

In an embodiment, the adaptor may adapt the goggle frame to have a different lens attachment mechanism, e.g., pin-lock. The adaptor also may increase a space between the lens and the user or provide a different field of view for the user. In another embodiment, the adaptor may adapt the goggle frame to have a different air flow or ventilation. Further, the adaptor may be compatible with goggle frames of various sizes styles and allow lenses or accessories interchangeable among goggle frames of various sizes and styles.

Figure 1:
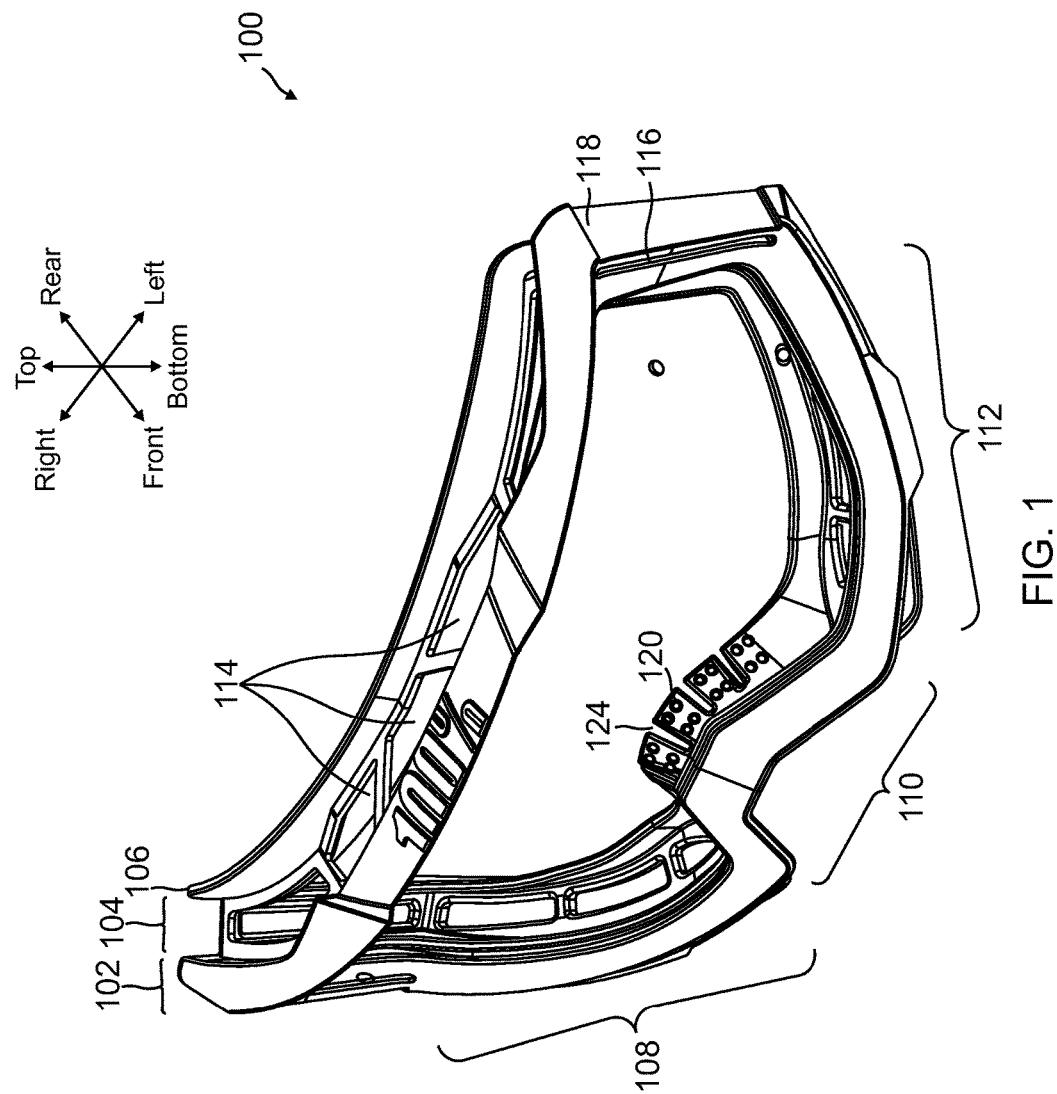
FIG. 1 shows a perspective front view of a goggle frame, in accordance with an embodiment.
Figure 2:
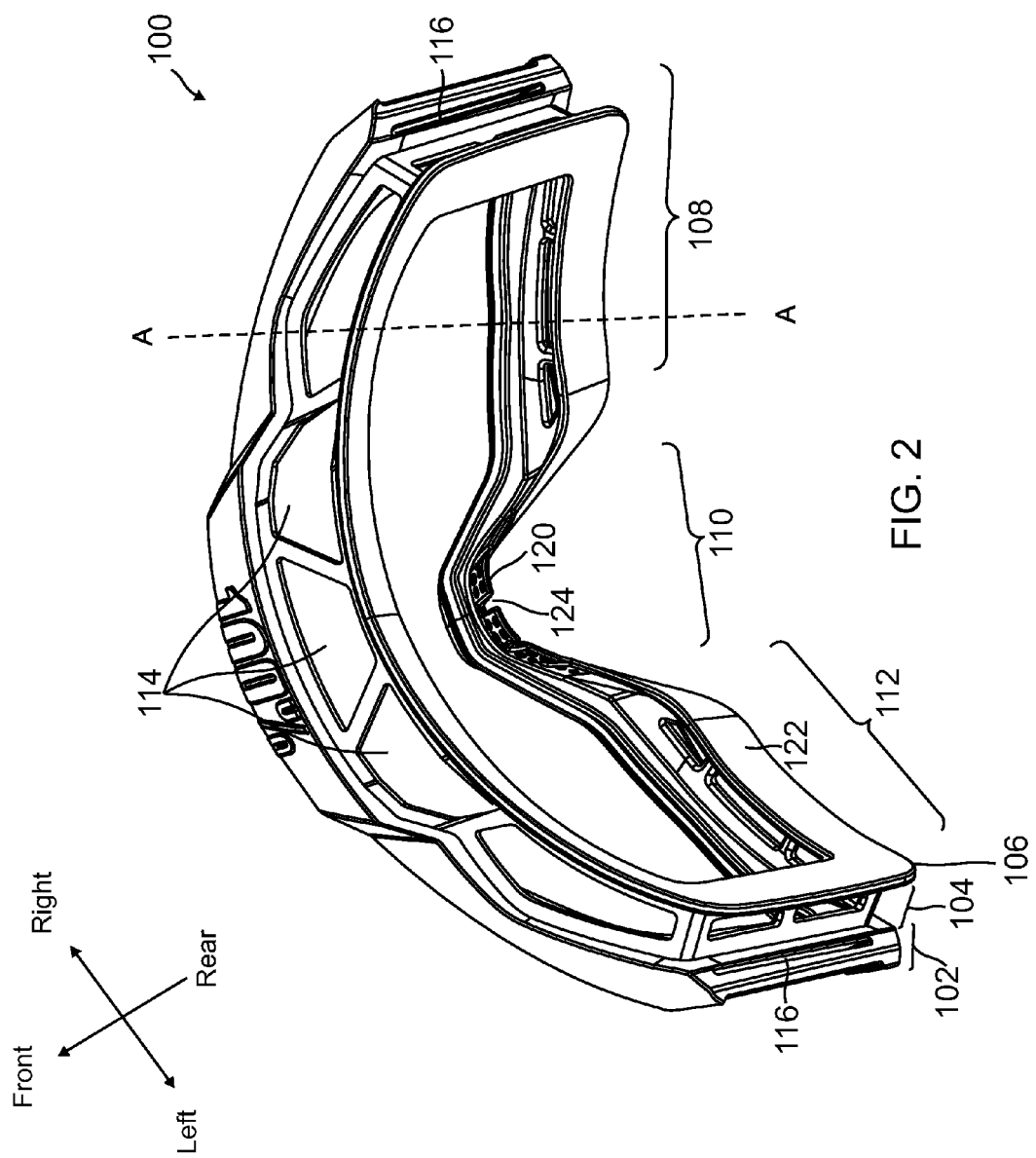
FIG. 2 shows a perspective rear view of the goggle frame of FIG. 1, in accordance with an embodiment.

FIGS. 1 and 2 show perspective front and rear views of a goggle frame 100, in accordance with an embodiment. As shown in FIGS. 1 and 2, goggle frame 100 may include a lens receiving portion 102, a ventilation portion 104, and a face plate 106. The lens receiving portion 102 may be configured to receive a lens and may be disposed substantially at a front end of goggle frame 100. The ventilation portion 104 may include a plurality of opening 114 configured to allow air to pass through to serve as a ventilation mechanism when the goggle frame is worn by a user. The ventilation portion 104 may connect the lens receiving portion 102 to the face plate 106.

The face plate 106 may be disposed at a rear end of goggle frame 100. The face plate 106 may be configured to rest on a user's face when the goggle frame 100 is worn by the user. In some embodiments, cushioning elements, such as foam pads, may be attached to the face plate 106 to provide additional comfort to the user when the face plate is rested on the face of the user. The goggle frame 100 may be formed with plastic resin material, such as a type of polycarbonate resin. The goggle frame 100 may be formed with plastic forming techniques, such as injection molding or the like.

Goggle frame 100 may have a loop shape with particular contours that may accommodate to the eyes and nose of a user. In particular, goggle frame 100 may include a right field vision region 108, a left field vision region 112, and a nose region 110. As shown in FIGS. 1 and 2, the right field vision region 108 may be configured to surround a right eye of a user, the left field vision region 112 may be configured to surround a left eye of the user, and the nose region 110 may be configured to rest on the nose of the user. In particular, the nose region 110 of the goggle frame 100 may have a dome shape to accommodate the nose of the user.

The lens receiving portion 102, the ventilation portion 104, and the face plate 106 may be formed continuously around the loop shape of the goggle frame 100. As such, the lens receiving portion 102, the ventilation portion 104, and the face plate 106 may have similar contours at the right field vision region 108, the nose region 110, and the left field vision region 112 of the goggle frame 100, respectively. As shown in FIG. 2, at the nose region 110, the face plate 106 and the ventilation portion 104 may merge. In particular, a facing surface 122 of the face plate 106 may gradually change from facing in the rear direction to facing in the downward direction at the dome shaped nose region 110 of the goggle frame 100. Thus, the face plate 106 may be configured to have a continuous and seamless contact with the face of the user around the user's eyes and around the user's nose. The face plate 106 may have cutouts 124 that may provide additional flexibility around the nose region 110 to provide additional comfort to the user. Further, the face plate 106 may have openings 120 around the nose region 110 to provide additional ventilation.

The lens receiving portion 102 may include slit openings 116 at the right end and the left end. The slit openings 116 may be configured to accommodate a goggle strap which may be used to wrap around a user's head to fasten the goggle frame 100 to the user. For example, two ends of the goggle strap may be threaded through the two slit openings 116, respectively. The lens receiving portion 102 also may include recesses 118 at the right and left ends near the slit openings 116. The recesses 118 may be configured to accommodate the goggle strap when the goggle strap wrap around the left and right sides of the goggle frame 100.

Figure 3:
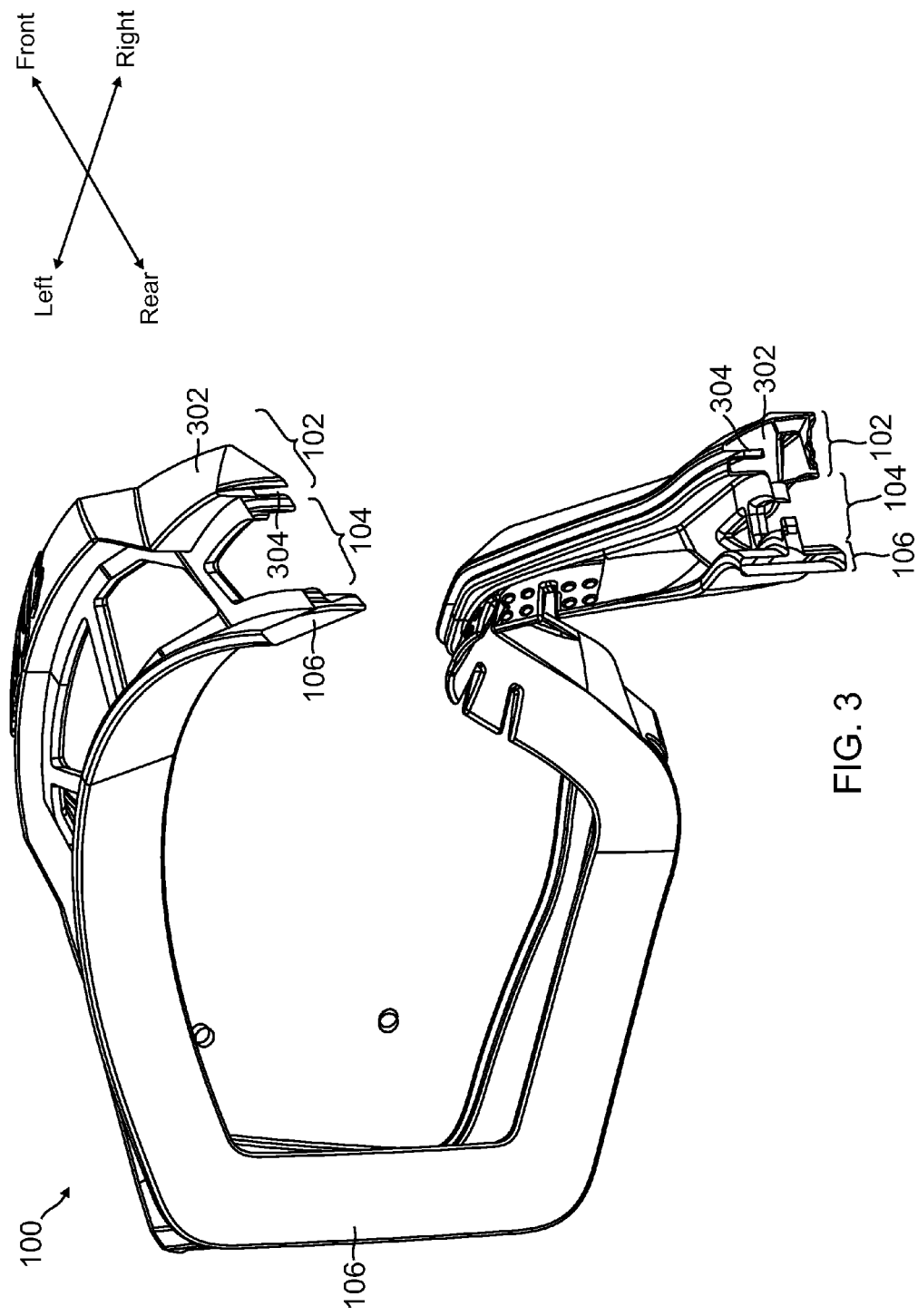
FIG. 3 shows the goggle frame of FIGS. 1 and 2 with a cut-away view along dashed line A-A in FIG. 2, in accordance with an embodiment.

FIG. 3 shows the goggle frame of FIGS. 1 and 2 with a cut-away view along dashed line A-A in FIG. 2, in accordance with an embodiment. As shown in FIG. 3, the lens receiving portion 102 may be connected to the face plate 106 by the ventilation portion 104. The lens receiving portion 102 may include a ridge 302 protruding from an inner side of the loop of the goggle frame 100. The ridge 302 may extend continuously around the loop of the goggle frame 100 substantially following the various contours of the loop. The shape or the contour of the lens receiving portion 102 may define the shape or contour of lens that may be received by the lens receiving portion 102. The lens receiving portion 102 may include a groove 304 formed on the ridge 302. The groove 304 may be formed continuously around the loop of the goggle frame 100 on the ridge 302. The groove 304 may be configured to accommodate a peripheral edge of a lens when the lens is attached to the goggle frame 100. A width of the groove 304 may define a thickness of the lens that may be received by the lens receiving portion 102.

Figure 4:
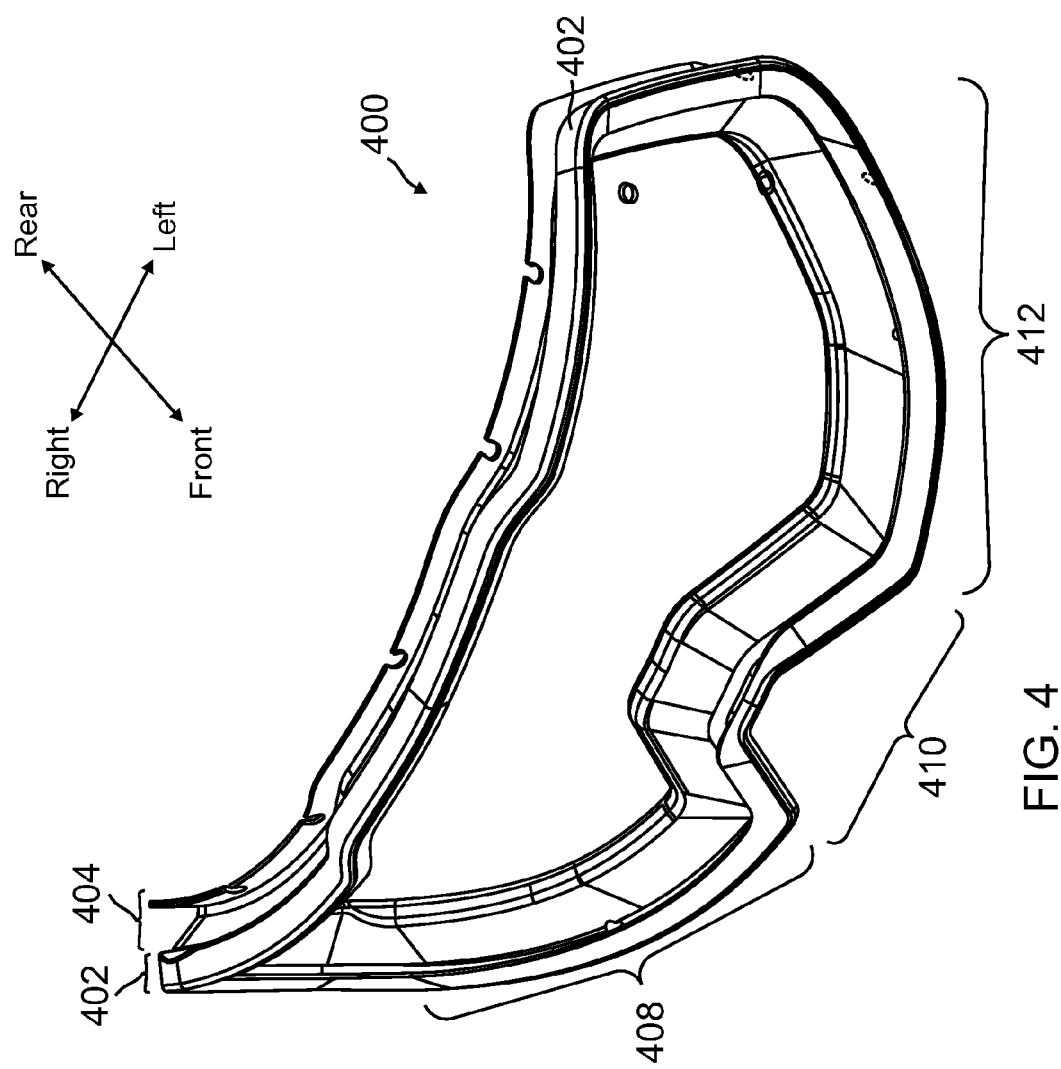
FIG. 4 shows a perspective front view of an adaptor, in accordance with an embodiment.
Figure 5:
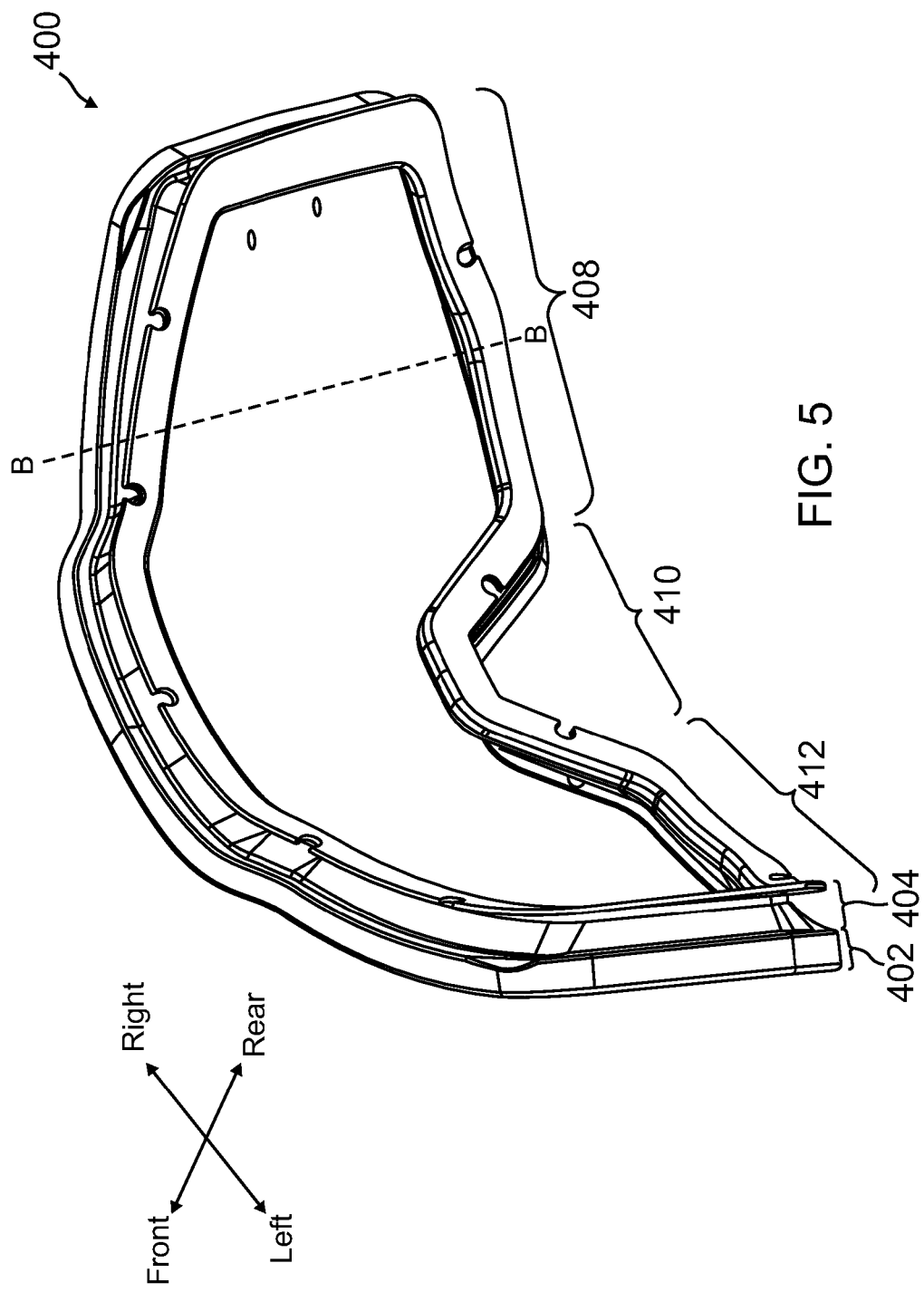
FIG. 5 shows a perspective rear view the adaptor of FIG. 4, in accordance with an embodiment.

FIGS. 4 and 5 show perspective front and rear views of an adaptor 400, in accordance with an embodiment. As shown in FIG. 4, the adaptor 400 may have a loop shape with a shape or contour that substantially corresponds to that of the goggle frame 100. The adaptor 400 may have a lens receiving portion 402 and an attachment portion 404. The lens receiving portion 402 may be configured to receive a lens. In particular, the lens received at the lens receiving portion 402 of the adaptor 400 may be different from the lens that is receivable by the lens receiving portion 102 of the goggle frame 100. For example, the lens that is receivable at the adaptor 400 and the lens that is receivable at the goggle frame 100 may differ in one or more of a size, a shape, a contour, a curvature, a prescription, a thickness, a tint, or the like. The attachment portion 404 of the adaptor 400 may be configured to attach to the lens receiving portion 102 of the goggle frame 100.

Similar to the goggle frame 100, the adaptor 400 may have a loop shape with particular contours that may accommodate to the eyes and nose of a user. In particular, the adaptor 400 may include a right field vision region 408, a left field vision region 412, and a nose region 410. As shown in FIGS. 4 and 5, the right field vision region 408 may be configured to surround a right eye of a user, the left field vision region 412 may be configured to surround a left eye of the user, and the nose region 410 may be configured to rest on the nose of the user. In particular, the nose region 410 of the adaptor 400 may have a dome shape to accommodate the nose of the user. The lens receiving portion 402 and the attachment portion 404 may be formed continuously around the loop shape of the adaptor 400. As such, the lens receiving portion 402, and the attachment portion 404 may have similar contours at the right field vision region 408, the nose region 410, and the left field vision region 412 of the adaptor 400, respectively.

Figure 6:
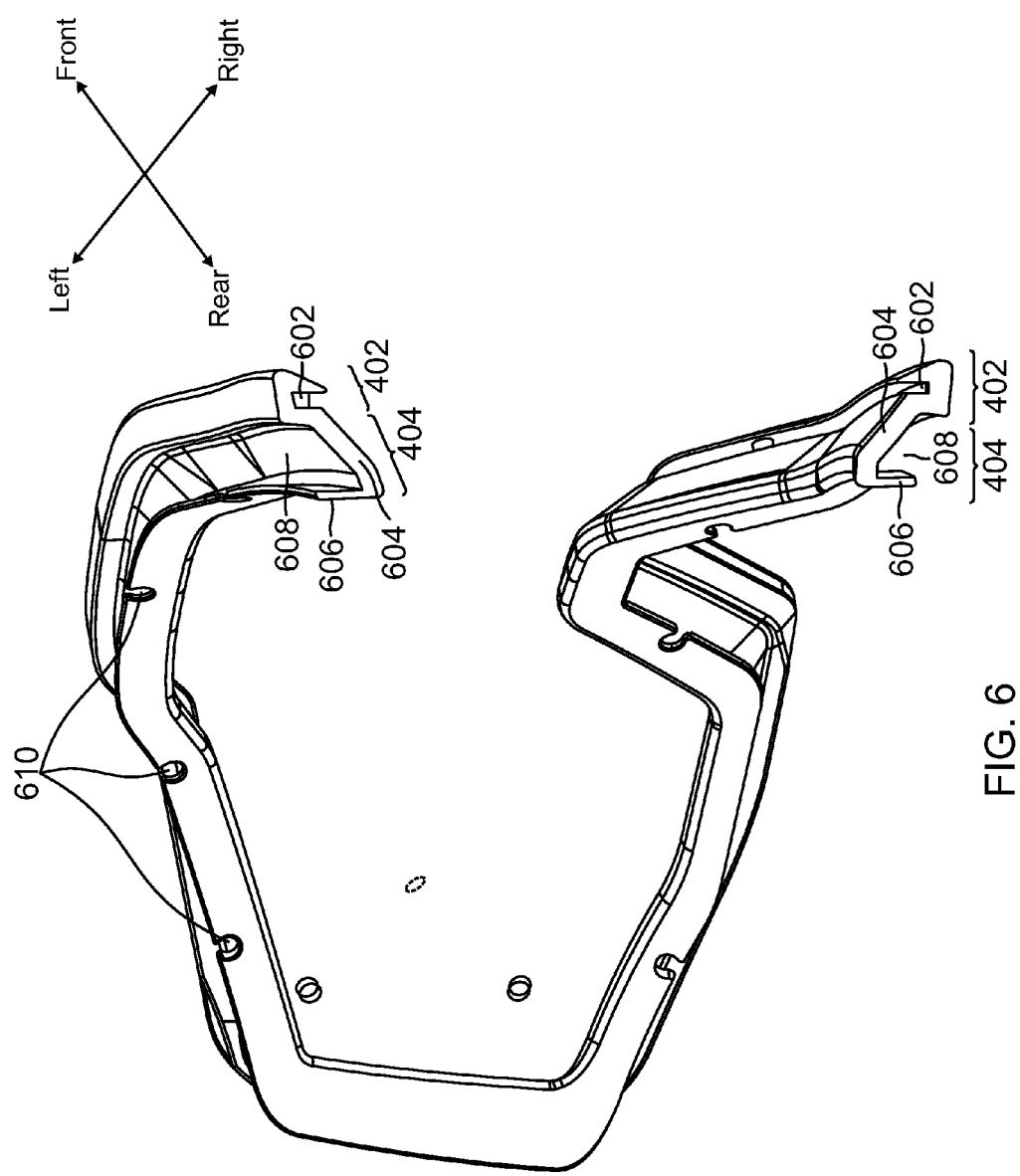
FIG. 6 shows the adaptor of FIGS. 4 and 5 with a cut-away view along dashed line B-B in FIG. 5, in accordance with an embodiment.

FIG. 6 shows the adaptor of FIGS. 4 and 5 with a cut-away view along dashed line B-B in FIG. 5, in accordance with an embodiment. As shown in FIG. 6, the lens receiving portion 402 may include a groove 602 formed at an inner side of the lens receiving portion 402. The groove 602 may be formed continuously around the loop of the adaptor 400 at the inner side of the lens receiving portion 402. The groove 602 may be configured to accommodate a peripheral edge of a lens when the lens is attached to the adaptor 400. A width of the groove 602 may define a thickness of the lens that may be received by the lens receiving portion 402.

The attachment portion 404 of the adaptor 400 may include a sloping wall 604 and a rib 606. The sloping wall 604 may slope from an inner and rear side of the lens receiving portion 402 in an inward and rearward direction toward the rib 606. The rib 606 and the slopping wall 604 may form a V-shaped recess 608 at an outer side of the loop of the adaptor 400. The rib 606 and the slopping wall 604 may be formed continuously around the loop of the adaptor 400. As such, the V-shaped recess 608 may extend continuously around the loop of the adaptor 400 at the outer side of the loop.

The rib 606 of the adaptor 400 may include a plurality of cutouts 610 at predetermined intervals around the loop. The cutouts 610 may provide additional flexibility or deformability to the rib 606 or to the adaptor 400 in general. The adaptor 400 may be formed with a type of plastic resin with certain flexibility or deformability. For example, the adaptor 400 may be formed with a type of polyurethane. In other embodiments, the adaptor 400 may be formed with one or more of a plastic material, a metal material, a composite material, and a biological material. In an embodiment, the adaptor 400 may be softer, has less rigidity, more flexible or deformable than the goggle frame 100. Thus, the adaptor 400 may be flexed or deformed to be fitted into the goggle frame 100. The adaptor 400 may be formed with injection molding. In other embodiments, the adaptor 400 may be formed with three-dimensional (3-D) printing.

Figure 7:
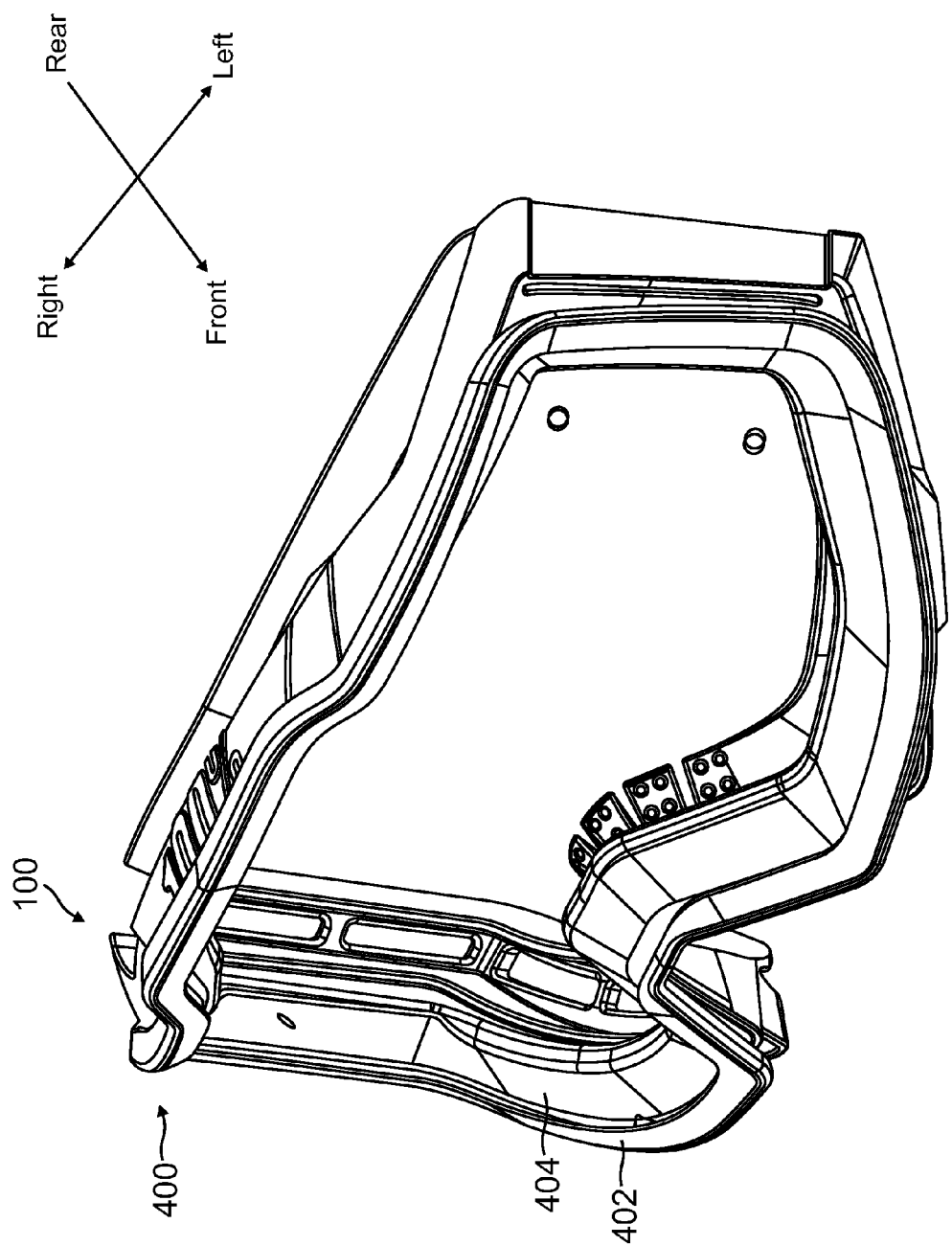
FIG. 7 shows a perspective front view of the adaptor of FIGS. 4, 5, and 6 attached to the goggle frame of FIGS. 1, 2, and 3, in accordance with an embodiment.
Figure 8:
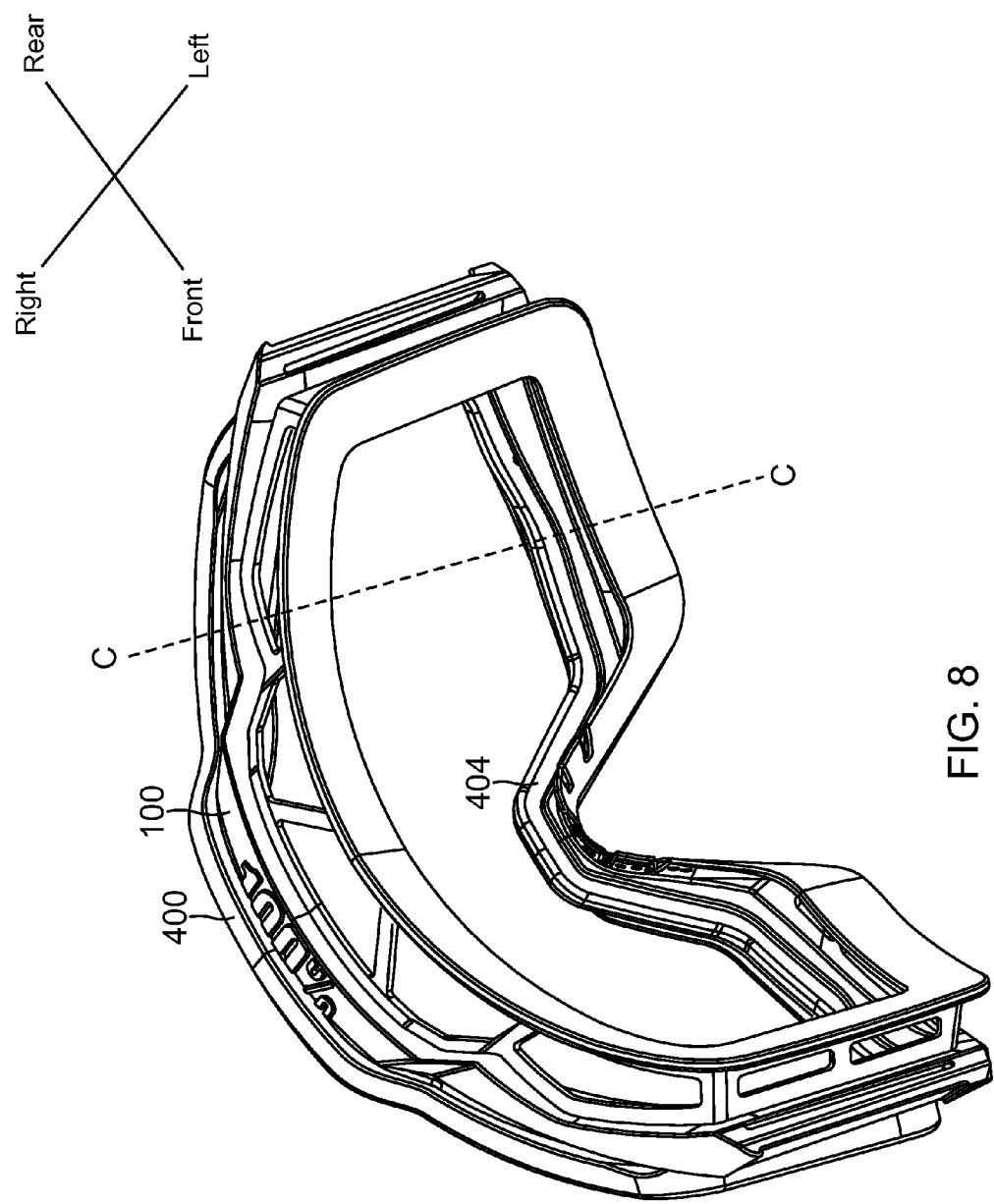
FIG. 8 shows a perspective rear view of the adaptor and the goggle frame of FIG. 7, in accordance with an embodiment.

FIGS. 7 and 8 show perspective front and rear views of the adaptor of FIGS. 4, 5, and 6 attached to the goggle frame of FIGS. 1, 2, and 3, in accordance with an embodiment. As shown in FIGS. 7 and 8, the adaptor 400 may be attached at a front side of the goggle frame 100. In particular, the attachment portion 404 of the adaptor 400 may engage with the lens receiving portion 102 of the goggle frame 100. The attachment portion 404 of the adaptor 400 may mount onto the lens receiving portion 102 of the goggle frame 100 from the inside of the loop of the goggle frame 100.

As shown in FIGS. 7 and 8, the right field vision region 408, the nose region 410, and the left field vision region 412 of the adaptor 400 may respectively correspond to the right field vision region 108, the nose region 110, and the left field vision region 112 of the goggle frame 100. As such, the vision field of the goggle frame 100 may coincide with the vision field of the adaptor 400. Thus, the user's field of view is not affected by the attachment of the adaptor 400 to the goggle frame 100.

Figure 9:
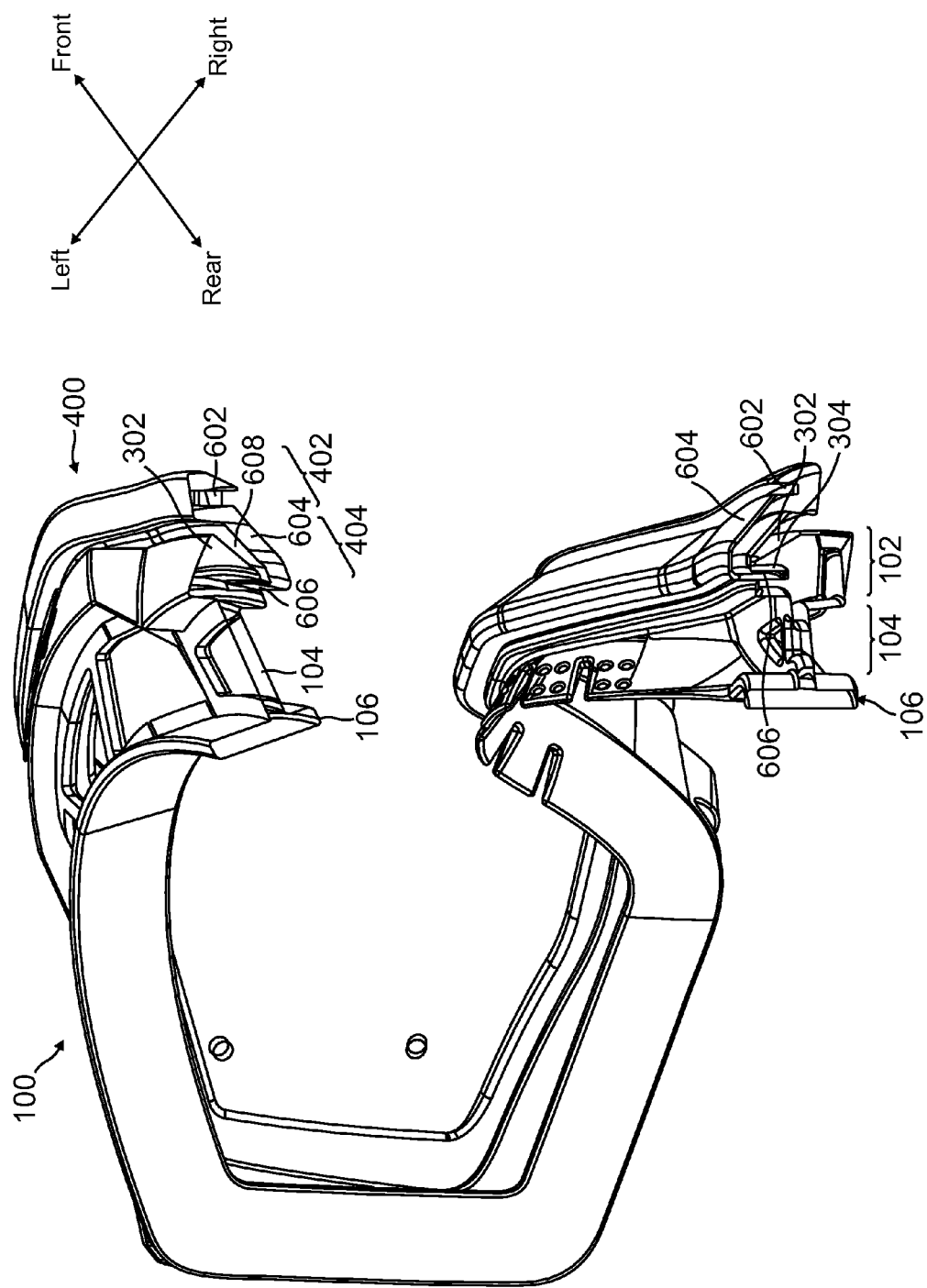
FIG. 9 shows the goggle frame and adaptor of FIGS. 7 and 8 with a cut-away view along dashed line C-C in FIG. 8, in accordance with an embodiment.

FIG. 9 shows the goggle frame and adaptor of FIGS. 7 and 8 with a cut-away view along dashed line C-C in FIG. 8, in accordance with an embodiment. As shown in FIG. 9, the attachment portion 404 of the adaptor 400 is attached to the lens receiving portion 102 of the goggle frame 100. In particular, attachment portion 404 of the adaptor 400 is mounted onto the ridge 302 of the goggle frame 100, such that a front portion of the ridge 302 is accommodated in the V-shaped recess 608 of the attachment portion 404. Further, the rib 606 is inserted into and accommodated in the groove 304 formed on the ridge 302 of the goggle frame 100. This engagement arrangement may be continuous around the loop of the goggle frame 100 when the adaptor 400 is attached to the goggle frame 100.

When the adaptor 400 is to be attached to the goggle frame 100, the adaptor 400 may be deformed or bent by a user. As noted above, the cutouts 610 formed on the rib 606 of the adaptor 400 may facilitate easier deformation or bending of the adaptor 400 during the attachment process. The adaptor 400 may be aligned with the goggle frame 100, such that the right field vision region 408, the nose region 410, and the left field vision region 412 of the adaptor 400 respectively correspond to the right field vision region 108, the nose region 110, and the left field vision region 112 of the goggle frame 100. The adaptor 400 may then be inserted within the goggle frame 100 by aligning and inserting the rib 606 of the adaptor 400 into the groove 304 of the goggle frame 100. The adaptor 400 then may be released to return to its original shape and be fitted into the lens receiving portion 102 of the goggle frame 100.

In order to remove the adaptor 400 from the goggle frame 100, a deformation or bending force is applied to the adaptor 400 to deform or bend the adaptor 400 to remove the adaptor 400. Thus, the relative rigidity of the adaptor 400 may retain the adaptor 400 within the lens receiving portion 102 of the goggle frame 100. Further, V-shaped recess 608 formed between the rib 606 and the sloping wall 604 may serve as a hook that fix the adaptor 400 on the ridge 302 of the goggle frame 100. Accordingly, the adaptor 400 may be retained at the goggle frame 100, unless a bending or deforming force is applied to the adaptor 400 to overcome the rigidity of the adaptor 400 to remove the adaptor 400 from the goggle frame 100.

Figure 10:
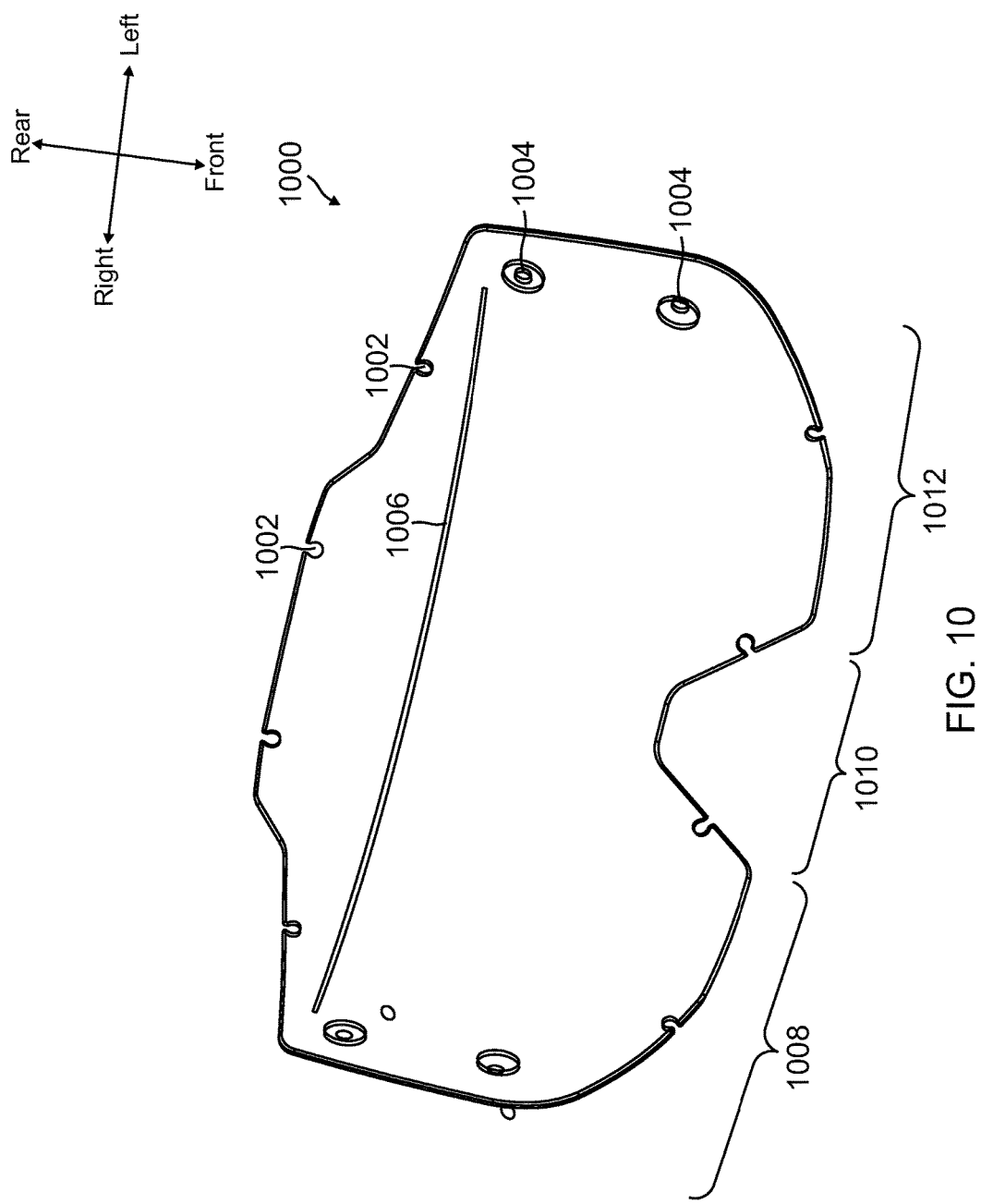
FIG. 10 shows a perspective front view of a lens, in accordance with an embodiment.

FIG. 10 shows a perspective front view of a lens, in accordance with an embodiment. As shown in FIG. 10, a lens 1000 may have a shape and curvature substantially corresponding to the loop shape of the adaptor 400. In particular, the loop shape of the groove 602 of the adaptor 400 may substantially define the shape and the peripheral contours of the lens 1000. The thickness of the lens 1000 may also correspond to the width of the groove 602 of the adaptor 400, such that the peripheral edge of the lens 1000 may be fitted into the groove 602 of the adaptor 400. The lens 1000 may include a plurality of cutouts 1002 formed on the peripheral edge of the lens 1000 at predetermined intervals along the peripheral of the lens 1000. The cutouts 1002 may provide additional flexibility or deformability to the lens 1000 that may allow the lens 1000 to be inserted into the adaptor 400 or the goggle frame 1000.

The lens 1000 also may include openings 1004 positioned at two ends of the lens 1000. The openings 1004 may be used to attach various accessories, such as roll-off film systems, to the lens 1000. The lens 1000 may include a rib 1006 provided across a front side of the lens 1000. A mud flap may be attached to the rib 1006 to provide mud or dirt shielding. Similar to the adaptor 400 or the goggle frame 100, the lens 1000 may a right field vision region 1008, a left field vision region 1012 and a nose region 1010.

When the lens 1000 is to be attached to the adaptor 400, the lens 1000 may be deformed or bent by a user. As noted above, the cutouts 1002 formed on the peripheral edge of the lens 1000 may facilitate easier deformation or bending of the lens 1000 during the attachment process. The lens 1000 may be aligned with the adaptor 400, such that the right field vision region 1008, the nose region 1010, and the left field vision region 1012 of the lens 1000 respectively correspond to the right field vision region 408, the nose region 410, and the left field vision region 412 of the adaptor 400. The lens 1000 may then be inserted within the adaptor 400 by aligning and inserting the peripheral edge of the lens 1000 into the groove 602 of the adaptor 400. The lens 1000 then may be released to return to its original shape and be fitted into the lens receiving portion 402 of the adaptor 400.

Figure 11:
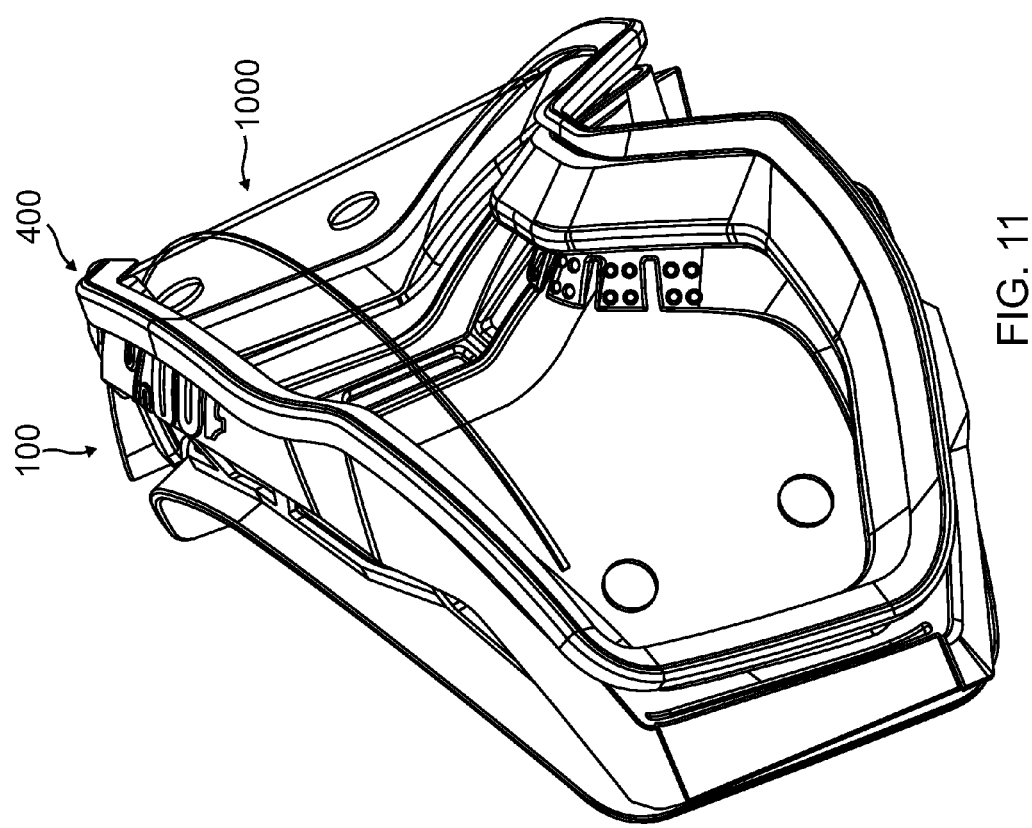
FIG. 11 shows a perspective view of an assembly of a goggle frame, an adaptor, and a lens, in accordance with an embodiment.

FIG. 11 shows a perspective view of an assembly of a goggle frame, an adaptor, and a lens, in accordance with an embodiment. As shown in FIG. 11, the adaptor 400 is attached to the goggle frame 100 and the lens 1000 is attached to the adaptor 400. As such, the goggle frame 100 may be adapted via adaptor 400 to use lenses of different sizes, shapes, curvatures, thicknesses, contours, and the like. The goggle frame 100 also may be adapted via adaptor 400 to use different accessories, such as imaging devices, display devices, lighting devices, various sensors, and the like. For example, the goggle frame 100, which is designed for use with a 30 mm roll-off film system, may be adapted via the adaptor 400 to use a 45 mm roll-off film system. In another embodiment, different tear-off film systems may be adapted via the adaptor 400.

Further, the adaptor 400 may increase a distance or clearance between the lens 1000 and the eyes of the user. In an embodiment, ventilation openings may be formed on the adaptor 400 to provide additional ventilations. In another embodiment, the adaptor 400 may include additional attachment mechanisms configured to attach to accessories, such as LCD, LED, or projected display device, cameras, lights, heads-up displays, GPS devices, and the like.

Figure 12:
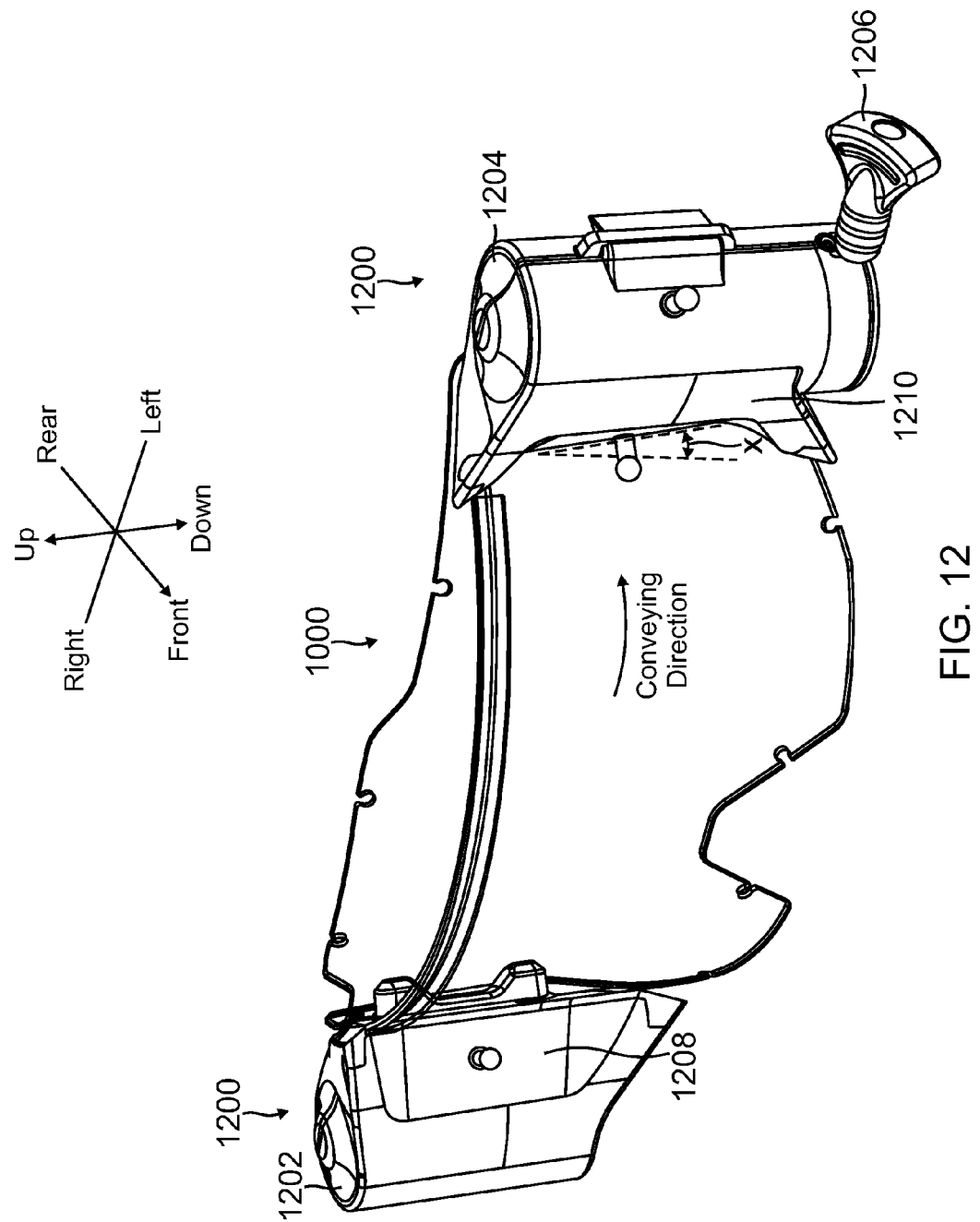
FIG. 12 shows a perspective front view of a lens attached with a roll-off film system, in accordance with an embodiment.
Figure 13:
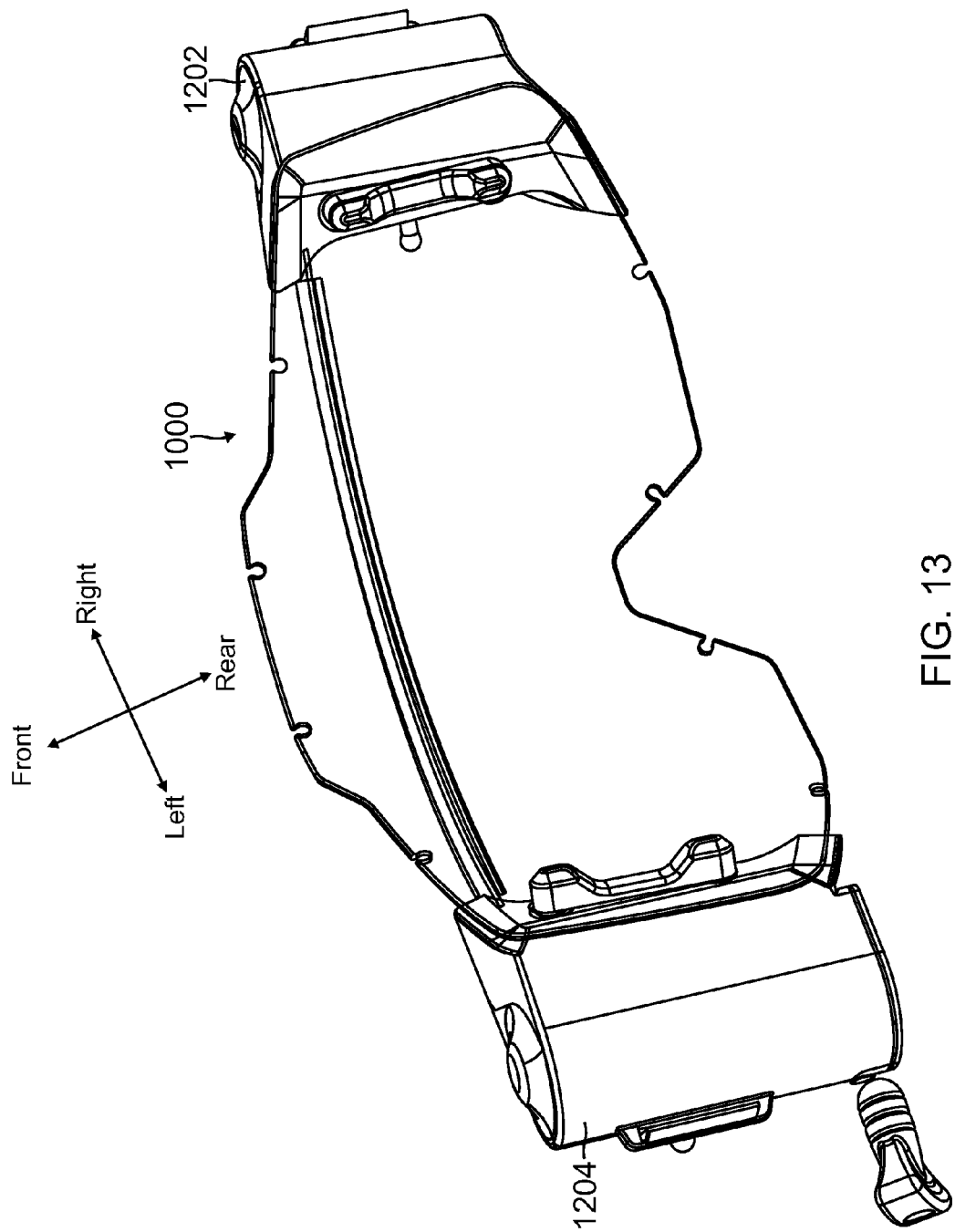
FIG. 13 shows a perspective rear view of a lens attached with a roll-off film system, in accordance with an embodiment.
Figure 14:
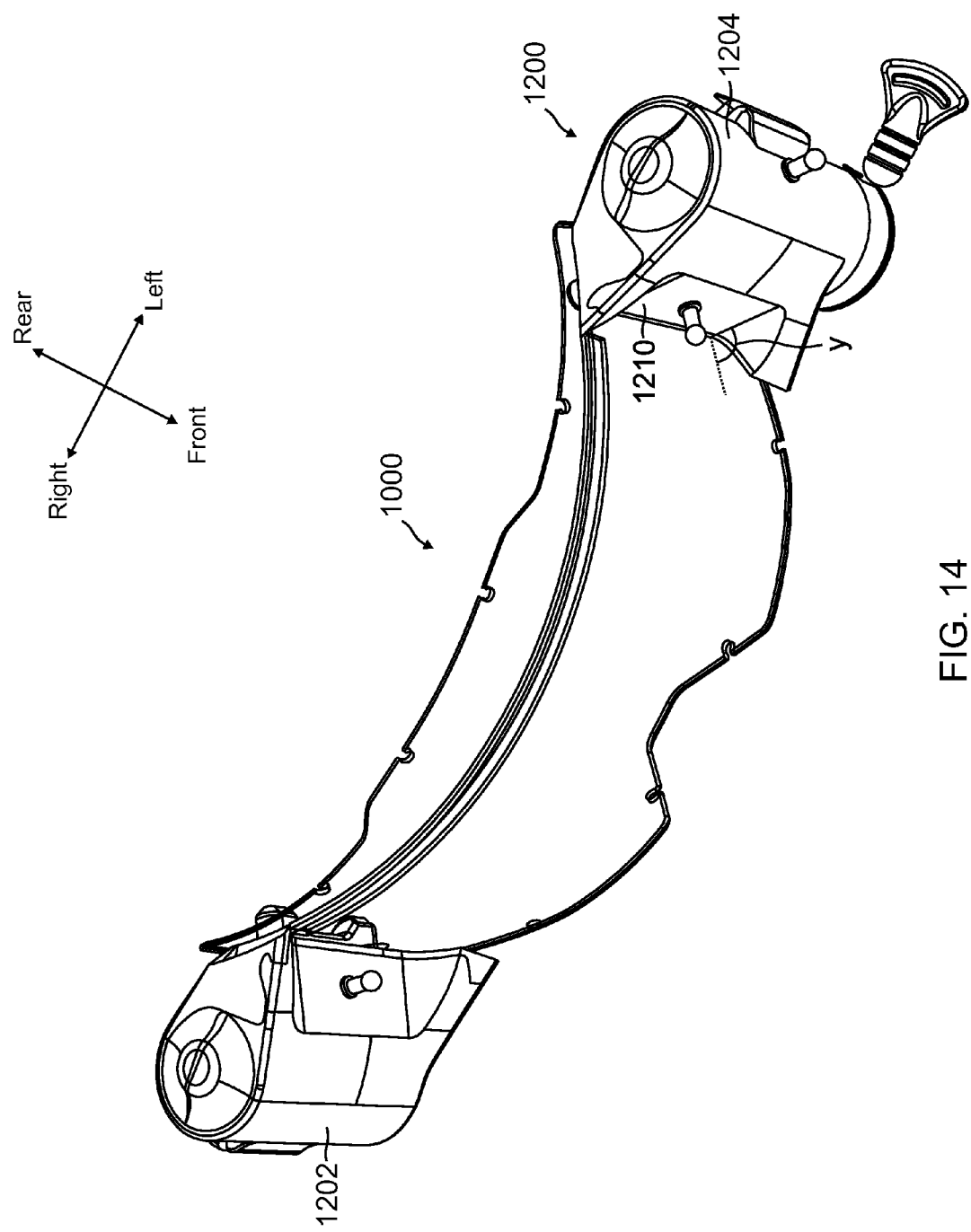
FIG. 14 shows a perspective top view of a lens attached with a roll-off film system, in accordance with an embodiment.

FIGS. 12, 13, and 14 show perspective front, rear, and top views of a lens attached with a roll-off film system, in accordance with an embodiment. As shown in FIGS. 12, 13, and 14, a roll-off film system 1200 may be attached to the lens 1000. The roll-off film system 1200 may include a film dispensing canister 1202 and a film receiving canister 1204. The film dispensing canister 1202 may be configured to store a roll of clear film and dispense the roll of clear film across the lens 1000. A section of the roll of the clear film may be stretched across the lens 1000 from the dispensing canister 1202 to the receiving canister 1204. The stretched clear film may rest on a front surface of the lens 1000. As shown in FIG. 13, the roll-off film system 1200 may be attached to the openings 1004 at the left and right end portions of the lens 1000.

The film dispensing canister 1202 may include a dispensing axle around which a roll of clear film is wound. The film receiving canister 1204 may include a receiving axle around which used sections of the clear film is wound. The film receiving canister 1204 may also include a ratchet system configured to drive the receiving axle to wind the used film into the film receiving canister 1204. The ratchet system may include a pull string 1206 operable by a user. The user may pull the pull string 1206 to drive the receiving axle to wind a section of clear film resting on the lens 1000 into the receiving canister 1204. The pull string 1206 may have a length corresponding to a winding distance of one lens width, such that one pull of the pull string 1206 may wind a section of clear film corresponding to a width of the lens 1000 into the film receiving canister 1204.

The ratchet system may include a spring configured to retract and rewound the pull string 1206 after it is pulled by the user. As such, after a pull by the user, the pull string 1206 may automatically be retracted or rewound into the receiving canister 1204 ready for winding the next section film. When the section of the film covering the lens 1000 becomes dirty or fill with dirt or debris due to sport or activities, the user may pull the pull string 1206 to retract the used or dirty section of the film into the film receiving canister 1204. As the used section of the film is retracted into the film receiving canister 1204, a new section of the film may be conveyed onto the lens 1000. Thus, the new section of the film may provide better field of view for the user to continue the sport or activities.

As shown in FIG. 12, the receiving canister 1204 may include a receiving blade 1210 configured to contact and guide the film into the receiving canister 1204. A top portion of the receiving blade 1210 may protrude more upstream in a conveying direction of the film on the lens 1000 than a lower portion of the receiving blade 1210. The receiving blade 1210 may be configured to remove dirt or debris from the film by sliding on the film when the film is conveyed into the receiving canister 1204. The dirt or debris may be collected at the receiving blade 1210. Because the top portion of the receiving blade 1210 protrudes more upstream in the conveying direction of the film than the lower portion of the receiving blade 1210, the edge of the receiving blade 1210 may form an angle x relative to a vertical or up-down direction. As such, the lower portion of the edge of the receiving blade 1210 may slope away to the left side of the lens 1000. The angled edge of the receiving blade 1210 may allow dirt or debris to fall off and away from the field of view of the lens 1000 due to gravity as more dirt or debris are collected at the receiving blade 1210.

As shown in FIG. 14, the receiving blade 1210 of the receiving canister 1204 may form a y angle with respect to a tangent line of the curve of the lens 1000. As such, the receiving blade 1210 may substantially act as a shovel to pick up and remove dirt or debris from the film as the film is conveyed into the receiving canister 1204. This feature may substantially reduce the amount of dirt or debris entering the receiving canister 1204 when the film is conveyed into the receiving canister 1204.

Figure 15:
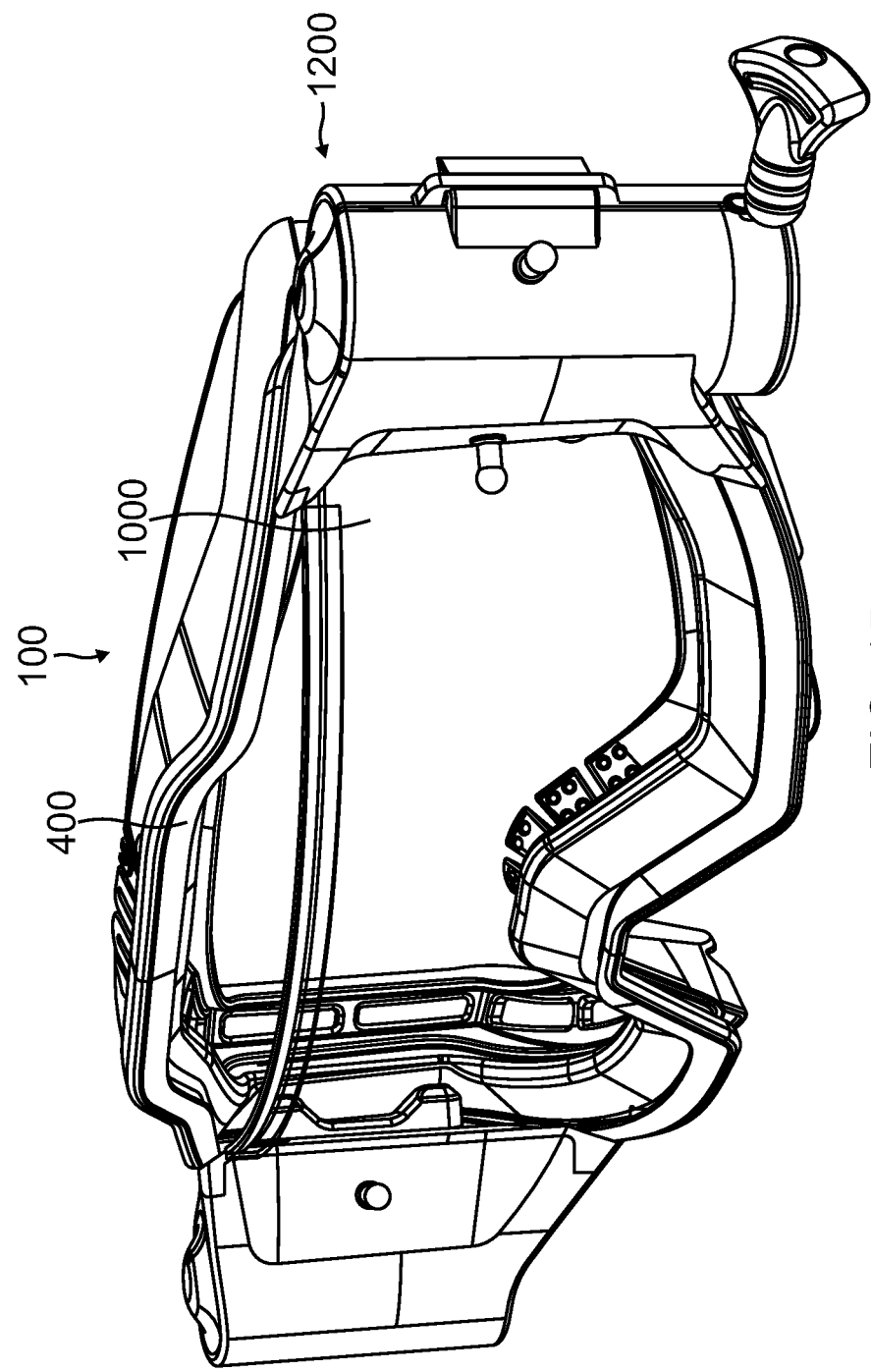
FIG. 15 shows a perspective front view of a goggle frame attached with an adaptor and a roll-off film system, in accordance with an embodiment.
Figure 16:
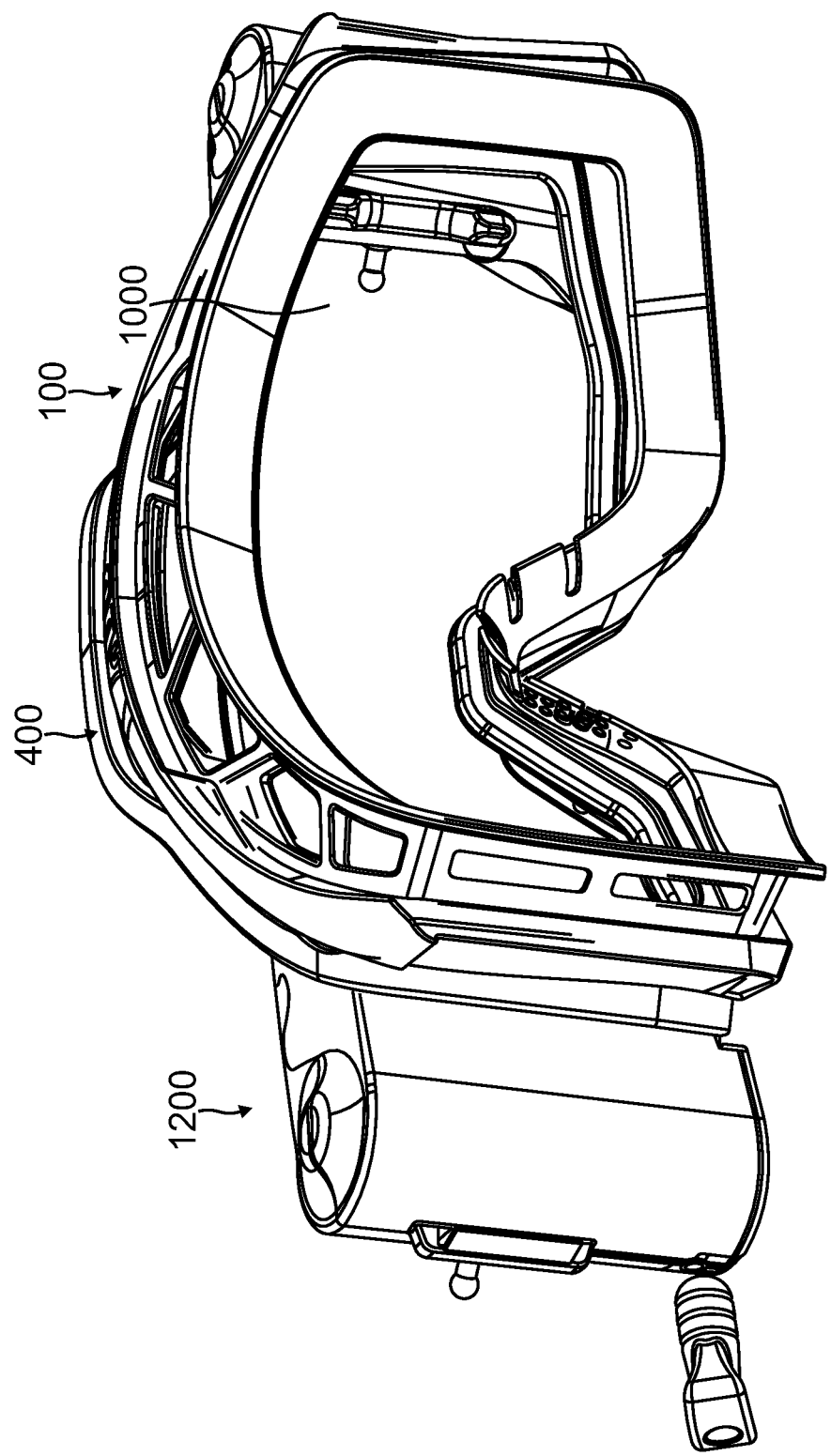
FIG. 16 shows a perspective rear view of a goggle frame attached with an adaptor and a roll-off film system, in accordance with an embodiment.

FIGS. 15 and 16 show perspective front and rear views of a goggle frame attached with an adaptor and a roll-off film system, in accordance with an embodiment. As shown in FIGS. 15 and 16, the goggle frame 100 is attached with the adaptor 400. The adaptor 400 is installed with the lens 1000 and the roll-off film system 1200 is installed on the lens 1000. As such, the goggle frame 100 may be adapted via the adaptor 400 to use a roll-off film system of different size. For example, the goggle frame 100 may be configured to receive a lens that is compatible with a 30 mm roll-off film system. The adaptor 400 may adapt the goggle frame 100 to receive a larger lens 1000 that is compatible with a 45 mm roll-off film system.

Figure 17:
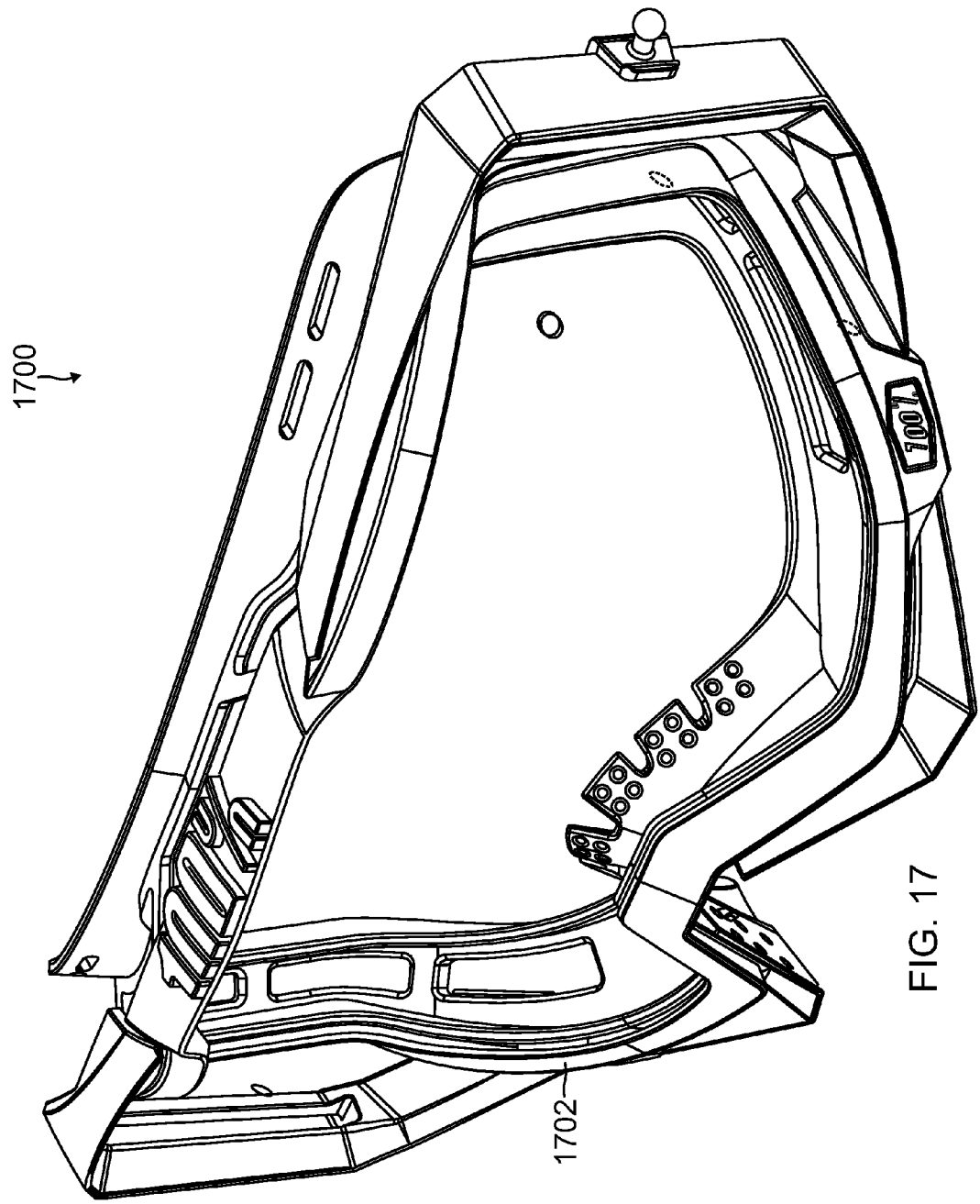
FIG. 17 shows a perspective front view of a goggle frame, in accordance with another embodiment.
Figure 18:
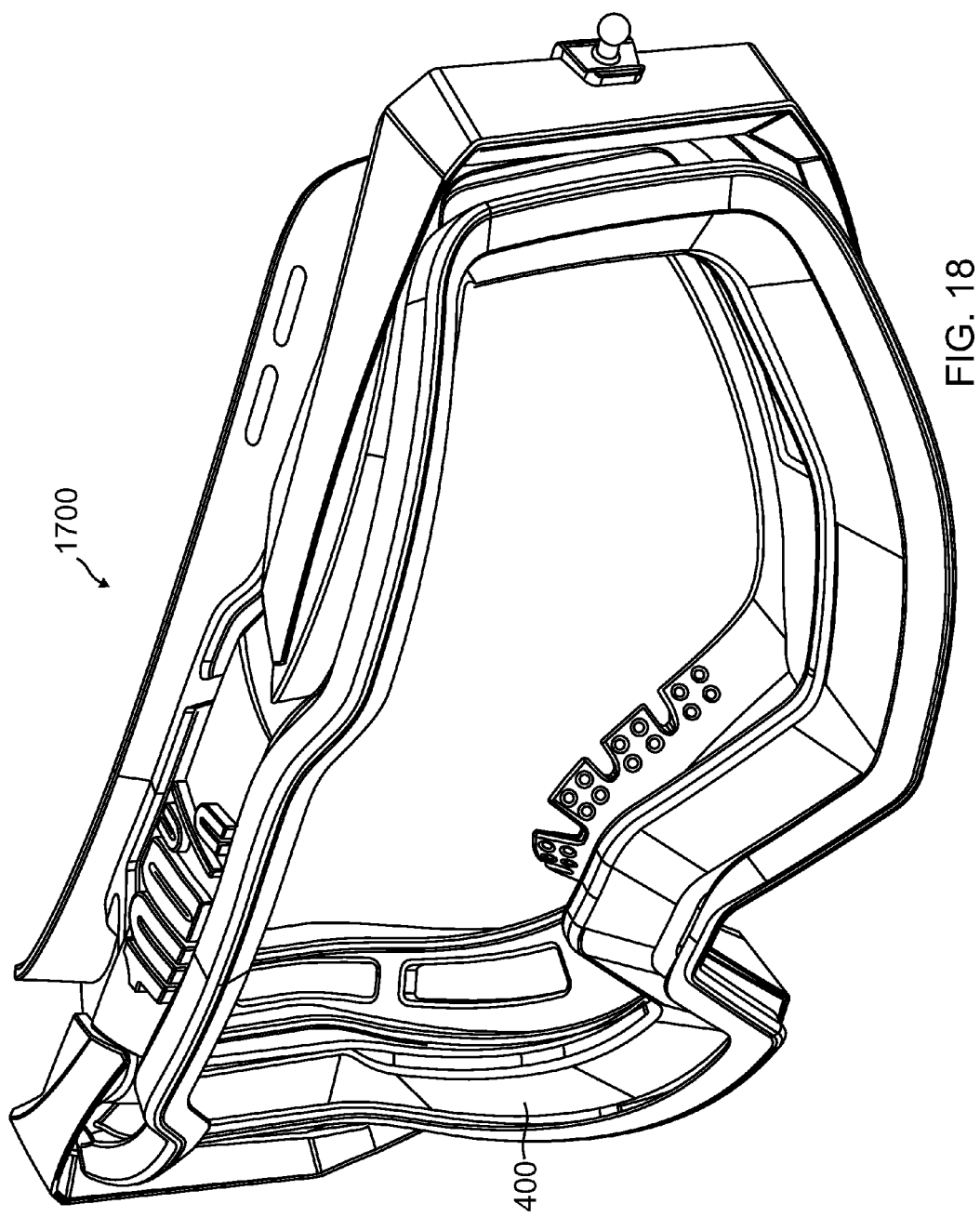
FIG. 18 shows a perspective front view of the goggle frame of FIG. 17 attached with an adaptor, in accordance with another embodiment.

FIG. 17 shows a perspective front view of a goggle frame, in accordance with another embodiment. As shown in FIG. 17, a goggle frame 1700 may have a different style or shape from that of the goggle frame 100. The adaptor 400 may be configured to attach to the goggle frame 1700. For example, the attachment portion 404 of the adaptor 400 may attach to a lens receiving portion 1702 of the goggle frame 1700. As shown in FIG. 18, the adaptor 400 is attached to the goggle frame 1700.

Figure 19:
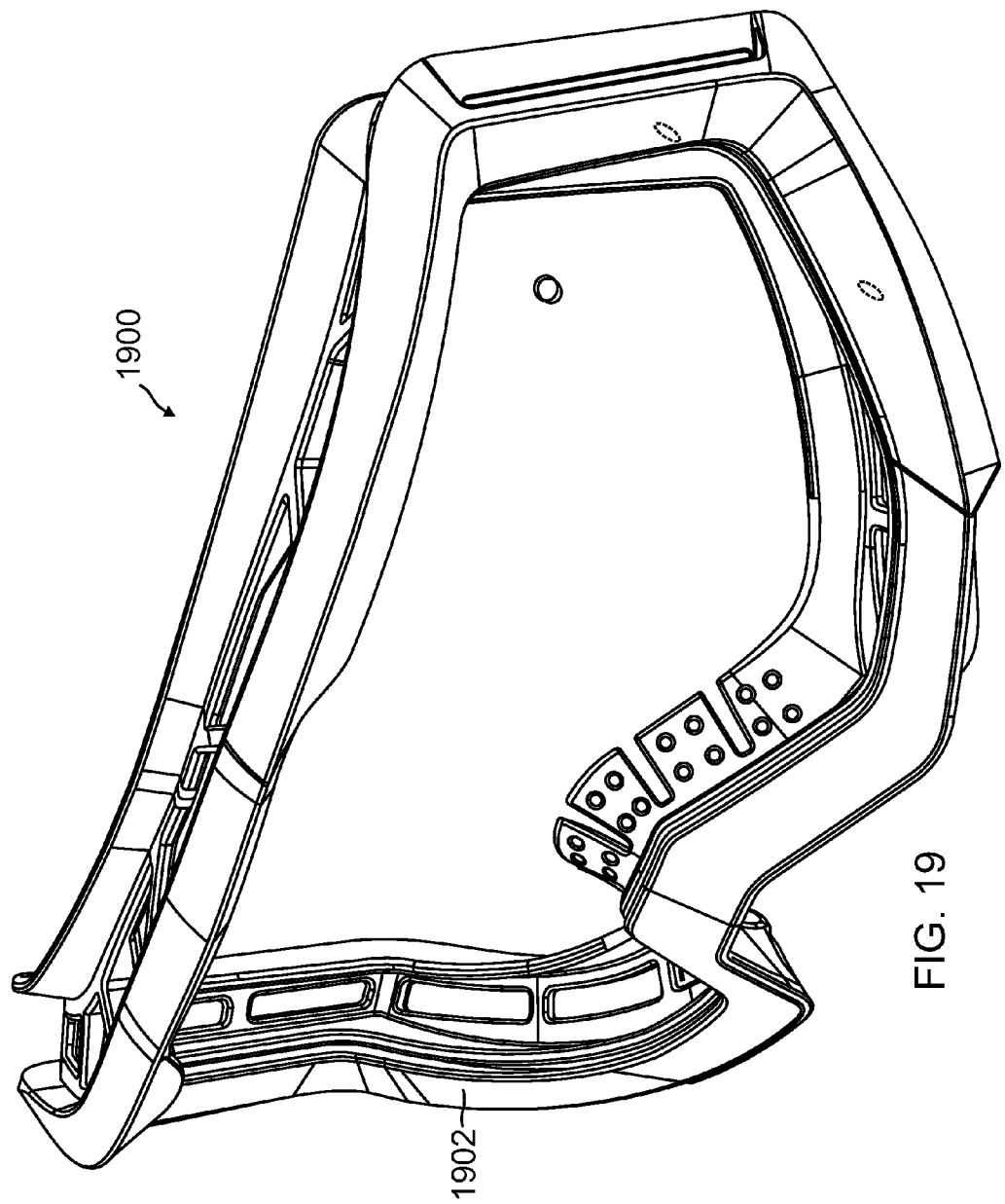
FIG. 19 shows a perspective front view of a goggle frame, in accordance with yet another embodiment.
Figure 20:
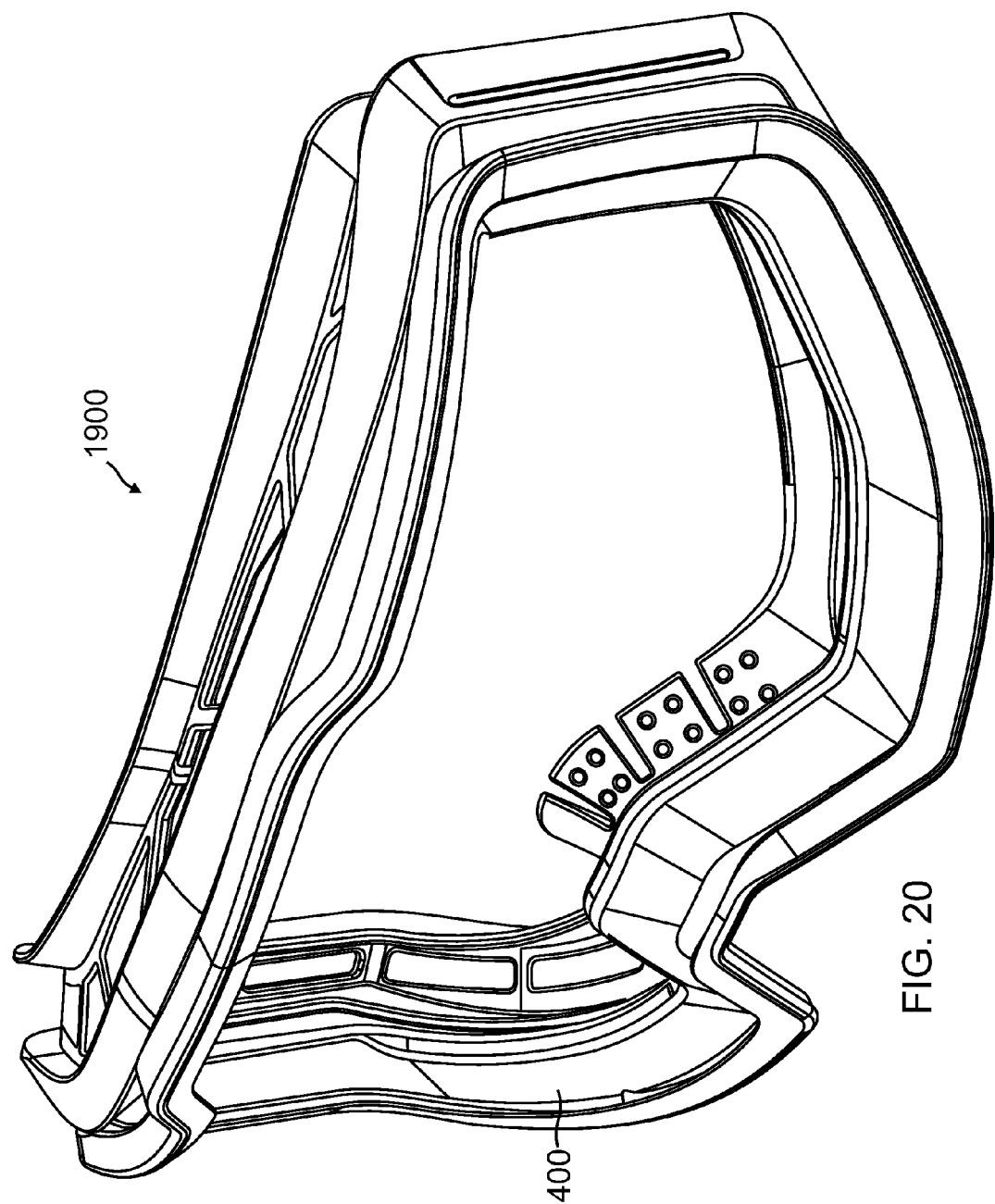
FIG. 20 shows a perspective front view of the goggle frame of FIG. 19 attached with an adaptor, in accordance with yet another embodiment.

Further, FIG. 19 shows a perspective front view of a goggle frame, in accordance with yet another embodiment. As shown in FIG. 19, a goggle frame 1900 may have a yet different style or shape from that of the goggle frame 100 and that of the goggle frame 1700. The adaptor 400 may be configured to attach to the goggle frame 1900. For example, the attachment portion 404 of the adaptor 400 may attach to a lens receiving portion 1902 of the goggle frame 1700. As shown in FIG. 20, the adaptor 400 is attached to the goggle frame 1900. Thus, the same adaptor 400 may be compatible with different styles of goggle frames. Accordingly, different styles of goggle frames may use the adaptor 400 to adapt to different lenses or accessories.

Figure 21:
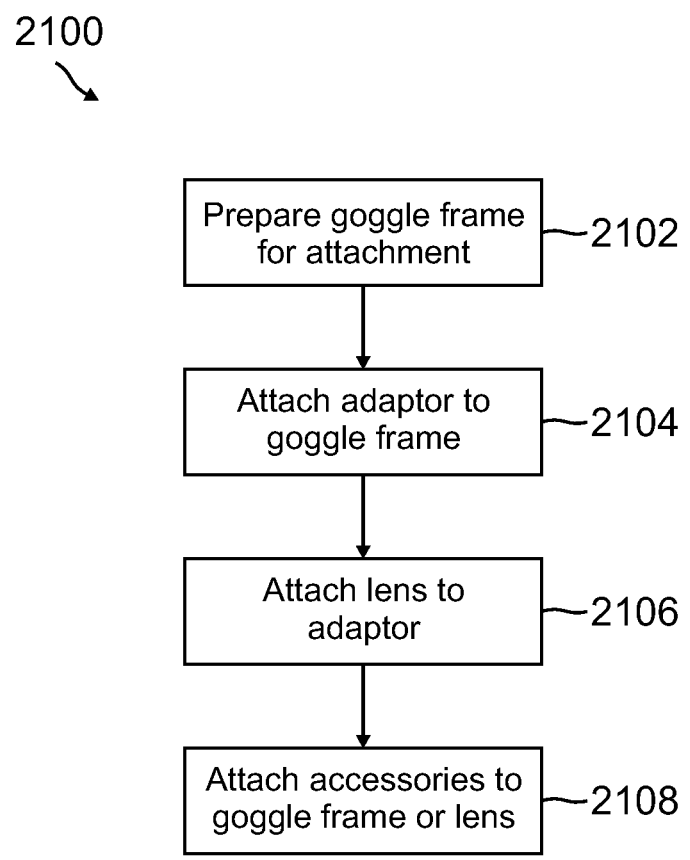
FIG. 21 shows a flow chart for a method of installing an adaptor to a goggle frame, in accordance with an embodiment.

FIG. 21 shows a flow chart for a method of installing an adaptor to a goggle frame, in accordance with an embodiment. As shown in FIG. 21, a method 2100 for utilizing a goggle adaptor with a goggle frame may be implemented. At step 2102, the goggle frame 100 may be prepared for attachment of the adaptor 100. For example, the original lens of the goggle frame 100 may be removed from the goggle frame. Further, a type of adaptor that is compatible with the goggle frame 100 may be determined. In addition, the desired lens or accessory to which the goggle frame is to be adapted to may also be determined. The type of adaptor also may be determined based on the desired lens or accessory that the goggle frame is to be adapted to.

At step 2104, a proper adaptor 400 may be selected and attached to the goggle frame 100. The proper adaptor 400 may be compatible with the goggle frame 100, e.g., receivable by the lens receiving portion 102 of the goggle frame 100. Further, the proper adaptor 400 may be configured to receive the desired lens or accessory. The adaptor 400 may be deform or bent and fitted into the lens receiving portion 102 of the goggle frame 100. In particular, the rib 606 of the adaptor 400 may be inserted into the groove 304 of the goggle frame 100, as shown in FIG. 9.

At step 2106, the lens 1000 may be attached to the adaptor 400. The lens 1000 may be inserted into the groove 602 of the adaptor 400. In particular, the lens 1000 may be deformed or bent to be fitted into the groove 602. At step 2108, the accessory, such as a roll-off film system 1200, may be attached to the lens 1000. In other embodiments, accessories, such as an imaging system, a lighting system, a sensor system, or the like may be attached to the adaptor 400. Accordingly, the adaptor 400 may be installed on the goggle frame 100 to adapt the goggle frame 100 to different lenses or accessories.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected is:

1. A goggle comprising:
   a goggle frame comprising a first lens receiving portion comprising a ridge formed continuously around the goggle frame and a first groove disposed proximate the ridge, wherein the first lens receiving portion is disposed at a front side of the goggle frame;
   an adaptor configured to detachably attach to the first lens receiving portion of the goggle frame, the adaptor comprising:
      a second lens receiving portion receiving a second lens, and
      an attachment portion extending from the second lens receiving portion, the attachment portion comprising a rib distal to the second lens receiving portion; and
   wherein in a first configuration the first lens receiving portion receives the first lens within the first groove and in a second configuration the first lens is removed and at least a portion of the rib distal to the second lens receiving portion is inserted into the first groove to attach the adaptor to the first lens receiving portion of the goggle frame to hold the adaptor to the goggle frame.

2. The goggle of claim 1, wherein the second lens receiving portion comprises a second groove wider than the first groove.

3. The goggle of claim 1, wherein the rib of the adaptor is continuously engaged around a loop of the first groove.

4. The goggle of claim 1, wherein the attachment portion further comprises a sloping wall proximal to the second lens receiving portion, the sloping wall and the rib forming a recess continuously around the adaptor, wherein the recess accommodates at least a portion of the ridge formed continuously around the goggle frame of the first lens receiving portion of the goggle frame when the adaptor is attached to the first lens receiving portion of the goggle frame.

5. The goggle of claim 1, wherein a thickness of the rib corresponds to a thickness of the first lens, and wherein the first groove comprises a width substantially similar to the thickness of the rib and the thickness of the first lens.

6. The goggle of claim 1, wherein the first groove is formed on the ridge continuously around the goggle frame at an inner side of the goggle frame, and wherein the rib of the adaptor is disposed continuously around an outer side of the adaptor.

7. The goggle of claim 4, wherein the sloping wall of the adaptor connects the rib to the second lens receiving portion of the adaptor.

8. The goggle of claim 1, wherein the goggle frame further comprises:

a face plate configured to rest on a face of a user; and
a ventilation portion disposed between the face plate and the first lens receiving portion, wherein the ventilation portion comprises a plurality of ventilation openings.

9. The goggle of claim 1, wherein the second lens receiving portion of the adaptor comprises a second groove formed continuously around the adaptor at an inner side of the adaptor, and wherein the second groove is configured to receive a peripheral edge of the second lens.

10. The goggle of claim 1, further comprising a roll-off film system attached to the second lens, wherein the roll-off film system is configured to convey a film across the second lens.

11. The goggle of claim 1, further comprising a tear-off film system attached to the second lens received at the adaptor.

12. A method of assembling the goggle of claim 1, the method comprising:

attaching, while in the second configuration, the adaptor to the first lens receiving portion of the goggle frame such that the portion of the rib of the adaptor is inserted into the first groove.

13. The method of claim 12, further comprising:

removing, before attaching the adaptor to the first lens receiving portion and while in the first configuration, the first lens from within the first groove; and
attaching an accessory to one of the second lens or the adaptor.

* * * * *